United States Patent
Conlon et al.

(10) Patent No.: US 10,172,684 B2
(45) Date of Patent: Jan. 8, 2019

(54) LIFECYCLE MONITORING FEATURES FOR SURGICAL INSTRUMENT

(71) Applicant: ETHICON LLC, Guaynabo, PR (US)

(72) Inventors: Sean P. Conlon, Loveland, OH (US); Lucas B. Elmer, Cincinnati, OH (US); Andrew W. Carroll, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 0 days.

(21) Appl. No.: 15/480,546

(22) Filed: Apr. 6, 2017

(65) Prior Publication Data

US 2017/0312044 A1 Nov. 2, 2017

Related U.S. Application Data

(60) Provisional application No. 62/329,381, filed on Apr. 29, 2016.

(51) Int. Cl.
*A61B 17/00* (2006.01)
*A61B 90/00* (2016.01)
(Continued)

(52) U.S. Cl.
CPC .......... *A61B 90/08* (2016.02); *A61B 17/295* (2013.01); *A61B 17/320068* (2013.01);
(Continued)

(58) Field of Classification Search
CPC ................. A61B 90/08; A61B 17/295; A61B 17/320092
(Continued)

(56) References Cited

U.S. PATENT DOCUMENTS

| 5,322,055 A | 6/1994 | Davison et al. |
| 5,324,299 A | 6/1994 | Davison et al. |

(Continued)

FOREIGN PATENT DOCUMENTS

| EP | 2 042 112 A2 | 4/2009 |
| EP | 2 510 891 A1 | 10/2012 |

(Continued)

OTHER PUBLICATIONS

International Search Report and Written Opinion dated Jan. 25, 2017 for Application No. PCT/US2016/055923, 11 pgs.

(Continued)

*Primary Examiner* — Kerri L McNally
(74) *Attorney, Agent, or Firm* — Frost Brown Todd LLC

(57) ABSTRACT

An apparatus includes a housing, a processing circuit, a user feedback feature, and a surgical instrument interface feature. The user feedback feature is in communication with the processing circuit. The surgical instrument interface feature includes a structural interface feature and an electrical interface feature. The structural interface feature is configured to fit in a portion of a body of a surgical instrument. The portion of the body of the surgical instrument is configured to receive an ultrasonic transducer. The electrical interface feature is in communication with the processing circuit and is configured to interface with a complementary electrical interface feature of the surgical instrument. The complementary electrical interface feature of the surgical instrument is configured to couple with an ultrasonic transducer. The processing circuit is configured to receive data relating to a number of uses of the surgical instrument via the electrical interface feature.

15 Claims, 18 Drawing Sheets

(51) Int. Cl.
*A61B 17/295* (2006.01)
*A61B 17/32* (2006.01)
*A61B 18/00* (2006.01)

(52) U.S. Cl.
CPC ........... *A61B 17/320092* (2013.01); *A61B 2017/00115* (2013.01); *A61B 2017/00119* (2013.01); *A61B 2017/00199* (2013.01); *A61B 2017/00477* (2013.01); *A61B 2017/00725* (2013.01); *A61B 2018/00988* (2013.01); *A61B 2090/0803* (2016.02); *A61B 2090/0807* (2016.02); *A61B 2560/028* (2013.01)

(58) Field of Classification Search
USPC ........................................................ 340/815.4
See application file for complete search history.

(56) References Cited

U.S. PATENT DOCUMENTS

| | | |
|---|---|---|
| 5,873,873 A | 2/1999 | Smith et al. |
| 5,897,523 A | 4/1999 | Wright et al. |
| 5,980,510 A | 11/1999 | Tsonton et al. |
| 5,989,264 A | 11/1999 | Wright |
| 6,063,098 A | 5/2000 | Houser et al. |
| 6,090,120 A | 7/2000 | Wright et al. |
| 6,165,191 A | 12/2000 | Shibata et al. |
| 6,283,981 B1 | 9/2001 | Beaupre |
| 6,309,400 B2 | 10/2001 | Beaupre |
| 6,325,811 B1 | 12/2001 | Messerly |
| 6,423,082 B1 | 7/2002 | Houser et al. |
| 6,454,782 B1 | 9/2002 | Schwemberger |
| 6,500,176 B1 | 12/2002 | Truckai et al. |
| 6,589,200 B1 | 7/2003 | Schwemberger et al. |
| 6,752,815 B2 | 6/2004 | Beaupre |
| 6,773,444 B2 | 8/2004 | Messerly |
| 6,783,524 B2 | 8/2004 | Anderson et al. |
| 6,887,252 B1 | 5/2005 | Okada et al. |
| 7,052,506 B2 | 5/2006 | Young et al. |
| 7,112,201 B2 | 9/2006 | Truckai et al. |
| 7,125,409 B2 | 10/2006 | Truckai et al. |
| 7,135,030 B2 | 11/2006 | Schwemberger et al. |
| 7,169,146 B2 | 1/2007 | Truckai et al. |
| 7,186,253 B2 | 3/2007 | Truckai et al. |
| 7,189,233 B2 | 3/2007 | Truckai et al. |
| 7,220,951 B2 | 5/2007 | Truckai et al. |
| 7,309,849 B2 | 12/2007 | Truckai et al. |
| 7,311,709 B2 | 12/2007 | Truckai et al. |
| 7,354,440 B2 | 4/2008 | Truckai et al. |
| 7,381,209 B2 | 6/2008 | Truckai et al. |
| 7,544,200 B2 | 6/2009 | Houser |
| 7,621,930 B2 | 11/2009 | Houser |
| 8,057,498 B2 | 11/2011 | Robertson |
| 8,142,461 B2 | 3/2012 | Houser et al. |
| 8,461,744 B2 | 6/2013 | Wiener et al. |
| 8,591,536 B2 | 11/2013 | Robertson |
| 8,623,027 B2 | 1/2014 | Price et al. |
| 8,663,220 B2 | 3/2014 | Wiener et al. |
| 8,911,460 B2 | 12/2014 | Neurohr et al. |
| 8,986,302 B2 | 3/2015 | Aldridge et al. |
| 9,023,071 B2 | 5/2015 | Miller et al. |
| 9,095,367 B2 | 8/2015 | Olson et al. |
| 9,381,058 B2 | 7/2016 | Houser et al. |
| 9,393,037 B2 | 7/2016 | Olson et al. |
| 9,408,622 B2 | 8/2016 | Stulen et al. |
| 2004/0097911 A1 | 5/2004 | Murakami et al. |
| 2006/0079874 A1 | 4/2006 | Faller et al. |
| 2007/0191713 A1 | 8/2007 | Eichmann et al. |
| 2007/0282333 A1 | 12/2007 | Fortson et al. |
| 2008/0200940 A1 | 8/2008 | Eichmann et al. |
| 2012/0078278 A1* | 3/2012 | Bales, Jr. ....... A61B 17/320092 606/169 |
| 2012/0116265 A1 | 5/2012 | Houser et al. |
| 2014/0151079 A1* | 6/2014 | Furui ................ B25F 5/02 173/46 |
| 2015/0080924 A1 | 3/2015 | Stulen et al. |
| 2015/0141981 A1 | 5/2015 | Price et al. |
| 2015/0148832 A1 | 5/2015 | Boudreaux et al. |
| 2015/0164532 A1 | 6/2015 | Faller et al. |
| 2015/0245850 A1 | 9/2015 | Hibner et al. |
| 2016/0015419 A1 | 1/2016 | Hibner et al. |
| 2016/0276856 A1* | 9/2016 | Miller .................. H02J 7/0042 |

FOREIGN PATENT DOCUMENTS

| | | |
|---|---|---|
| EP | 2 641 552 A2 | 9/2013 |
| EP | 2 692 297 A2 | 2/2014 |
| EP | 2 992 842 A1 | 3/2016 |
| WO | WO 00/78237 A1 | 12/2000 |

OTHER PUBLICATIONS

International Search Report and Written Opinion dated Mar. 8, 2017 for Application No. PCT/US2016/055926, 18 pgs.
U.S. Appl. No. 61/410,603, filed Nov. 5, 2010.
U.S. Appl. No. 62/242,440, filed Oct. 16, 2015.
U.S. Appl. No. 62/263,102, filed Dec. 4, 2015.
U.S. Appl. No. 62/329,381, filed Apr. 29, 2016.
U.S. Appl. No. 14/258,179, filed Apr. 22, 2014.
U.S. Appl. No. 15/270,540, filed Sep. 20, 2016.
U.S. Appl. No. 15/270,600, filed Sep. 20, 2016.
International Search Report and Written Opinion dated Aug. 22, 2017 for Application No. PCT/US2017/029274, 15 pgs.

* cited by examiner

LIFECYCLE MONITORING FEATURES FOR SURGICAL INSTRUMENT

PRIORITY

This application claims priority to U.S. Provisional Pat. App. No. 62/329,381, entitled "Apparatus to Provide Reusability of Ultrasonic Surgical Instrument Feature," filed Apr. 29, 2016, the disclosure of which is incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include one or more piezoelectric elements that convert electrical power into ultrasonic vibrations, which are communicated along an acoustic waveguide to the blade element. The precision of cutting and coagulation may be controlled by the operator's technique and adjusting the power level, blade edge angle, tissue traction, and blade pressure. The power level used to drive the blade element may be varied (e.g., in real time) based on sensed parameters such as tissue impedance, tissue temperature, tissue thickness, and/or other factors. Some instruments have a clamp arm and clamp pad for grasping tissue with the blade element.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," issued Nov. 9, 1999, the disclosure of which is incorporated by reference herein; U.S. Pat. No. 6,283,981, entitled "Method of Balancing Asymmetric Ultrasonic Surgical Blades," issued Sep. 4, 2001, the disclosure of which is incorporated by reference herein; U.S. Pat. No. 6,309,400, entitled "Curved Ultrasonic Blade having a Trapezoidal Cross Section," issued Oct. 30, 2001, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,423,082, entitled "Ultrasonic Surgical Blade with Improved Cutting and Coagulation Features," issued Jul. 23, 2002, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; U.S. Pat. No. 8,057,498, entitled "Ultrasonic Surgical Instrument Blades," issued Nov. 15, 2011, the disclosure of which is incorporated by reference herein; U.S. Pat. No. 8,461,744, entitled "Rotating Transducer Mount for Ultrasonic Surgical Instruments," issued Jun. 11, 2013, the disclosure of which is incorporated by reference herein; U.S. Pat. No. 8,591,536, entitled "Ultrasonic Surgical Instrument Blades," issued Nov. 26, 2013, the disclosure of which is incorporated by reference herein; U.S. Pat. No. 8,623,027, entitled "Ergonomic Surgical Instruments," issued Jan. 7, 2014, the disclosure of which is incorporated by reference herein; and U.S. Pat. No. 8,911,460, entitled "Ultrasonic Surgical Instruments," issued Dec. 16, 2014, the disclosure of which is incorporated by reference herein; and U.S. Pat. No. 9,023,071, entitled "Ultrasonic Device for Fingertip Control," issued May 5, 2015, the disclosure of which is incorporated by reference herein.

Still further examples of ultrasonic surgical instruments are disclosed in U.S. Pub. No. 2006/0079874, entitled "Clamp pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; and U.S. Pub. No. 2008/0200940, entitled "Ultrasonic Device for Cutting and Coagulating," published Aug. 21, 2008, the disclosure of which is incorporated by reference herein.

Some ultrasonic surgical instruments may include a cordless transducer such as that disclosed in U.S. Pat. No. 9,381,058, entitled "Recharge System for Medical Devices," issued Jul. 5, 2016, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pat. No. 9,393,037, issued Jul. 19, 2016, entitled "Surgical Instruments with Articulating Shafts," the disclosure of which is incorporated by reference herein; and U.S. Pat. No. 9,095,367, published Aug. 4, 2015, entitled "Flexible Harmonic Waveguides/Blades for Surgical Instruments," the disclosure of which is incorporated by reference herein.

Some instruments are operable to seal tissue by applying radiofrequency (RF) electrosurgical energy to the tissue. An example of a surgical instrument that is operable to seal tissue by applying RF energy to the tissue is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Some instruments are capable of applying both ultrasonic energy and RF electrosurgical energy to tissue. Examples of such instruments are described in U.S. Pub. No. 2015/0141981, entitled "Ultrasonic Surgical Instrument with Electrosurgical Feature," published May 21, 2015, now U.S. Pat. No. 9,949,785, issued Apr. 24, 2018, the disclosure of which is incorporated by reference herein; and U.S. Pat. No. 8,663,220, entitled "Ultrasonic Electrosurgical Instruments," issued Mar. 4, 2014, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
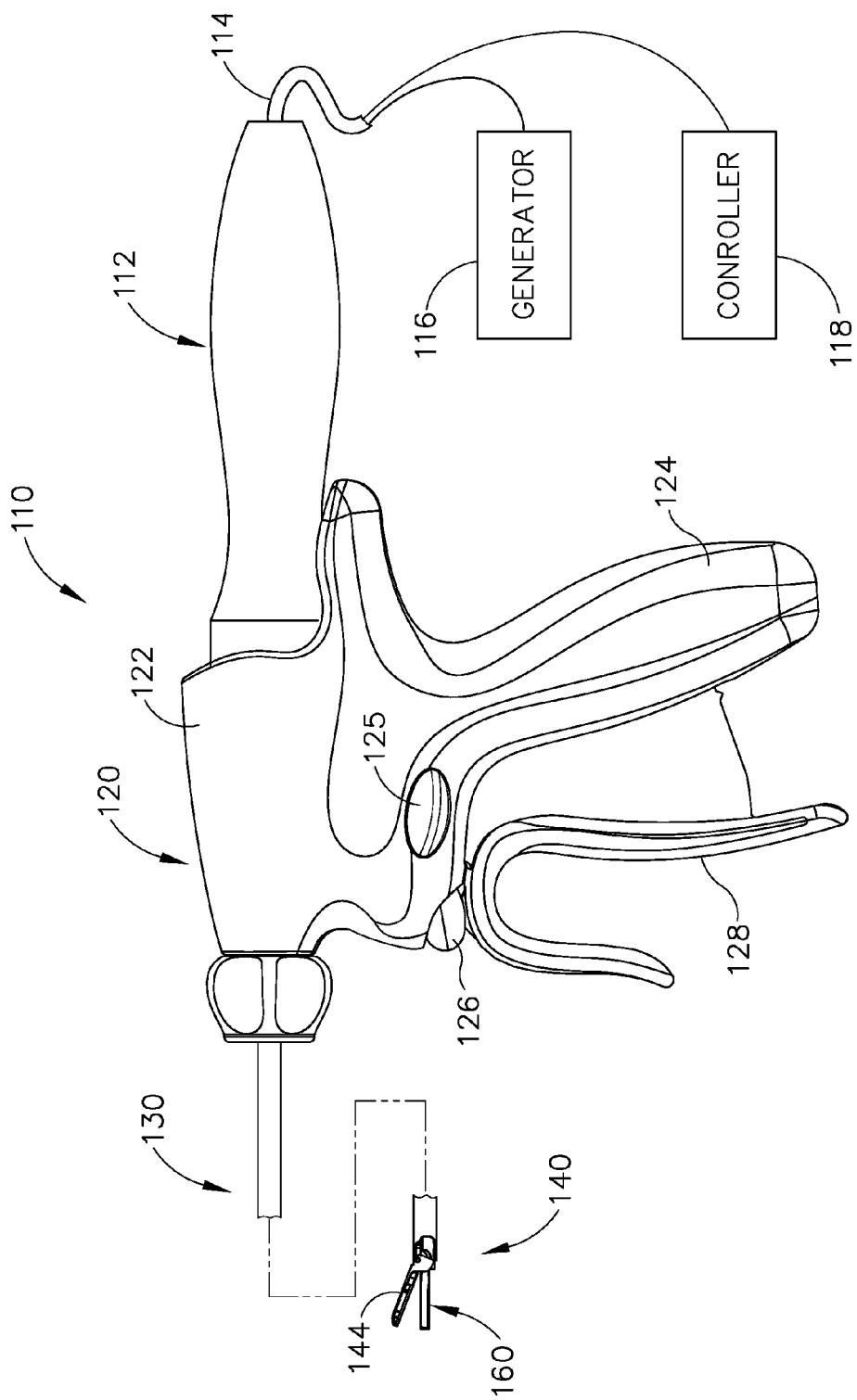
FIG. 1 depicts a side elevational view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument with Integrated RF Energy

FIG. 1 illustrates an exemplary ultrasonic surgical instrument (110). At least part of instrument (110) may be constructed and operable in accordance with at least some of the teachings of any of the patent references that are cited herein. As described therein and as will be described in greater detail below, instrument (110) is operable to cut tissue and seal or weld tissue (e.g., a blood vessel, etc.) substantially simultaneously. It should also be understood that instrument (110) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades.

Instrument (110) of the present example comprises a handle assembly (120), a shaft assembly (130), and an end effector (140). Handle assembly (120) comprises a body (122) including a pistol grip (124) and a pair of buttons (125, 126). Handle assembly (120) also includes a trigger (128) that is pivotable toward and away from pistol grip (124). It should be understood, however, that various other suitable configurations may be used, including but not limited to a scissor grip configuration. End effector (140) includes an ultrasonic blade (160) and a pivoting clamp arm (144). Clamp arm (144) is coupled with trigger (128) such that clamp arm (144) is pivotable toward ultrasonic blade (160) in response to pivoting of trigger (128) toward pistol grip (124); and such that clamp arm (144) is pivotable away from ultrasonic blade (160) in response to pivoting of trigger (128) away from pistol grip (124). Various suitable ways in which clamp arm (144) may be coupled with trigger (128) are disclosed in various patent references cited herein; and further suitable ways in which clamp arm (144) may be coupled with trigger (128) will be apparent to those of ordinary skill in the art in view of the teachings herein. In some versions, one or more resilient members are used to bias clamp arm (144) and/or trigger (128) to the open position shown in FIG. 1.

An ultrasonic transducer assembly (112) extends proximally from body (122) of handle assembly (120) in the present example. In some other versions, transducer assembly (112) is fully integrated within body (122). Transducer assembly (112) is coupled with a generator (116) via a cable (114). Transducer assembly (112) receives electrical power from generator (116) and converts that electrical power into ultrasonic vibrations through piezoelectric principles as is known in the art. Generator (116) cooperates with a controller (118) to provide a power profile to transducer assembly (112) that is particularly suited for the generation of ultrasonic vibrations through transducer assembly (112). While controller (118) is represented by a box that is separate from generator (116) in FIG. 1, controller (118) and generator (116) may be integrated together in a single unit. By way of example only, generator (116) may comprise a GEN04 or GEN11 sold by Ethicon Endo-Surgery, Inc. of Cincinnati, Ohio. In addition, or in the alternative, generator (116) may be constructed in accordance with at least some of the teachings of U.S. Pat. No. 8,986,302, entitled "Surgical Generator for Ultrasonic and Electrosurgical Devices," issued Mar. 24, 2015, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

End effector (140) of the present example comprises clamp arm (144) and ultrasonic blade (160). Clamp arm (144) includes a clamp pad that is secured to the underside of clamp arm (144), facing blade (160). By way of example only, the clamp pad may be formed of a polytetrafluoroethylene (PTFE) material and/or any other suitable material(s). By way of further example only, the clamp pad may be further constructed and operable in accordance with at least some of the teachings of U.S. Pat. No. 7,544,200, entitled "Combination Tissue Pad for Use with an Ultrasonic Surgical Instrument," issued Jun. 9, 2009, the disclosure of which is incorporated by reference herein.

Clamp arm (144) is operable to selectively pivot toward and away from blade (160) to selectively clamp tissue between clamp arm (144) and blade (160) in response to pivoting of trigger (128) toward pistol grip (124). Blade (160) of the present example is operable to vibrate at ultrasonic frequencies to effectively cut through and seal tissue, particularly when the tissue is being clamped between clamp arm (144) and blade (160). Blade (160) is positioned at the distal end of an acoustic drivetrain that includes an acoustic waveguide (not shown) and transducer assembly (112) to vibrate blade (160). By way of example only, the acoustic waveguide and blade (160) may comprise components sold under product codes SNGHK and SNGCB by Ethicon Endo-Surgery, Inc. of Cincinnati, Ohio. By way of further example only, the acoustic waveguide and blade (160) may be constructed and operable in accordance with the teachings of U.S. Pat. No. 6,423,082, entitled "Ultrasonic Surgical Blade with Improved Cutting and Coagulation Features," issued Jul. 23, 2002, the disclosure of which is incorporated by reference herein. As another merely illustrative example, the acoustic waveguide and blade (160) may be constructed and operable in accordance with the teachings of U.S. Pat. No. 5,324,299, entitled "Ultrasonic Scalpel Blade and Methods of Application," issued Jun. 28, 1994, the disclosure of which is incorporated by reference herein. Other suitable properties and configurations that may be used for the acoustic waveguide and blade (160) will be apparent to those of ordinary skill in the art in view of the teachings herein.

In the present example, the distal end of blade (160) is located at a position corresponding to an anti-node associated with resonant ultrasonic vibrations communicated through a flexible acoustic waveguide, to tune the acoustic assembly to a preferred resonant frequency $f_o$ when the acoustic assembly is not loaded by tissue. When transducer assembly (112) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 50 kHz or 55.5 kHz. When transducer assembly (112) of the present example is activated, these mechanical oscillations are transmitted through waveguides to reach blade (160), thereby providing oscillation of blade (160) at the resonant ultrasonic frequency. Thus, when tissue is secured between blade (160) and clamp arm (144), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (144) to also cauterize the tissue. For instance, blade (160) and clamp arm (144) may be configured to apply radiofrequency (RF) electrosurgical energy to tissue in addition to being configured to apply ultrasonic energy to tissue.

End effector (140) of the present example is further operable to apply radiofrequency (RF) electrosurgical energy to tissue that is captured between clamp arm (144) and blade (160). By way of example only, end effector (140) may include a single electrode that cooperates with a conventional ground pad that is secured to the patient, such that end effector (140) applies monopolar RF electrosurgical energy to the tissue. As another merely illustrative example, clamp arm (144) may include two electrodes that are operable to apply bipolar RF electrosurgical energy to the tissue. As yet another merely illustrative example, clamp arm (144) may include a single electrode and ultrasonic blade (160) may serve as a return path, such that ultrasonic blade (160) cooperates with the electrode of clamp arm (144) to apply bipolar RF electrosurgical energy to the tissue. In addition to or as an alternative to the foregoing, end effector (140) may be constructed and operable in accordance with at least some of the teachings of U.S. Pat. No. 8,663,220, entitled "Ultrasonic Electrosurgical Instruments," issued Mar. 4, 2014, the disclosure of which is incorporated by reference herein. Other suitable arrangements will be apparent to those of ordinary skill in the art in view of the teachings herein.

Instrument (110) may provide the operator with various ways in which to selectively apply only ultrasonic energy to tissue via end effector (140), only RF electrosurgical energy to tissue via end effector (140), or some combination of ultrasonic energy and RF electrosurgical energy to tissue via end effector (140). In versions where end effector (140) is operable to apply a combination of ultrasonic energy and RF electrosurgical energy to tissue, end effector (140) may be configured to apply ultrasonic energy and RF electrosurgical energy to tissue simultaneously. In addition, or in the alternative, in versions where end effector (140) is operable to apply a combination of ultrasonic energy and RF electrosurgical energy to tissue, end effector (140) may be configured to apply ultrasonic energy and RF electrosurgical energy to tissue in a sequence. Such a sequence may be predetermined; or may be based on sensed tissue conditions (e.g., tissue temperature, density, thickness, etc.). Various suitable control algorithms that may be used are disclosed in U.S. Pub. No. 2015/0141981, entitled "Ultrasonic Surgical Instrument with Electrosurgical Feature," published May 21, 2015, now U.S. Pat. No. 9,949,785, issued Apr. 24, 2018, the disclosure of which is incorporated by reference herein. It should also be understood that the control of ultrasonic energy and RF electrosurgical energy may be provided in accordance with at least some of the teachings of U.S. Pat. No. 8,663,220, entitled "Ultrasonic Electrosurgical Instruments," issued Mar. 4, 2014, the disclosure of which is incorporated by reference herein.

Buttons (125, 126) may provide the operator with varied control of the energy that is applied to tissue through end effector (140). For instance, in some versions, button (125) may be activated to apply RF electrosurgical energy to tissue; while button (126) may be activated to apply ultrasonic energy to tissue. As another merely illustrative example, button (125) may be activated to apply ultrasonic energy to tissue at a low power level (e.g., without also applying RF electrosurgical energy to tissue, applying RF electrosurgical energy to tissue simultaneously, or applying RF electrosurgical energy to tissue in a sequence with the ultrasonic energy); while button (126) may be activated to apply ultrasonic energy to tissue at a high power level (e.g., without also applying RF electrosurgical energy to tissue, applying RF electrosurgical energy to tissue simultaneously, or applying RF electrosurgical energy to tissue in a sequence with the ultrasonic energy). In addition, or in the alternative, buttons (125, 126) may provide functionality in accordance with at least some of the teachings of U.S. Pub. No. 2015/0141981, entitled "Ultrasonic Surgical Instrument with Electrosurgical Feature," published May 21, 2015, now U.S. Pat. No. 9,949,785, issued Apr. 24, 2018 the disclosure of which is incorporated by reference herein. Other suitable ways in which buttons (125, 126) may provide operation of instrument (110) will be apparent to those of ordinary skill in the art in view of the teachings herein.

II. Exemplary Ultrasonic Surgical Instrument with Combination of Reusable and Disposable Components In some instances, it may be desirable to provide a version of instrument (110) that is formed by a combination of components that are disposable (e.g., configured for use in only one surgical procedure) and components that are reusable (e.g., configured for use in more than one surgical procedure, subject to reprocessing and sterilization, etc., between surgical procedures). By way of example only, the disposable and reusable components of a surgical instrument may be assembled together to form the surgical instrument before a surgical procedure, the assembled surgical instrument may then be used to perform the surgical procedure, and then the disposable and reusable components of the surgical instrument may be disassembled after the surgical procedure is complete. Providing a disposable/reusable dichotomy among surgical instrument components may provide a reduction in cost and overall waste as compared to conventional instrumentations that are provided as an entirely disposable unit.

Figure 2:
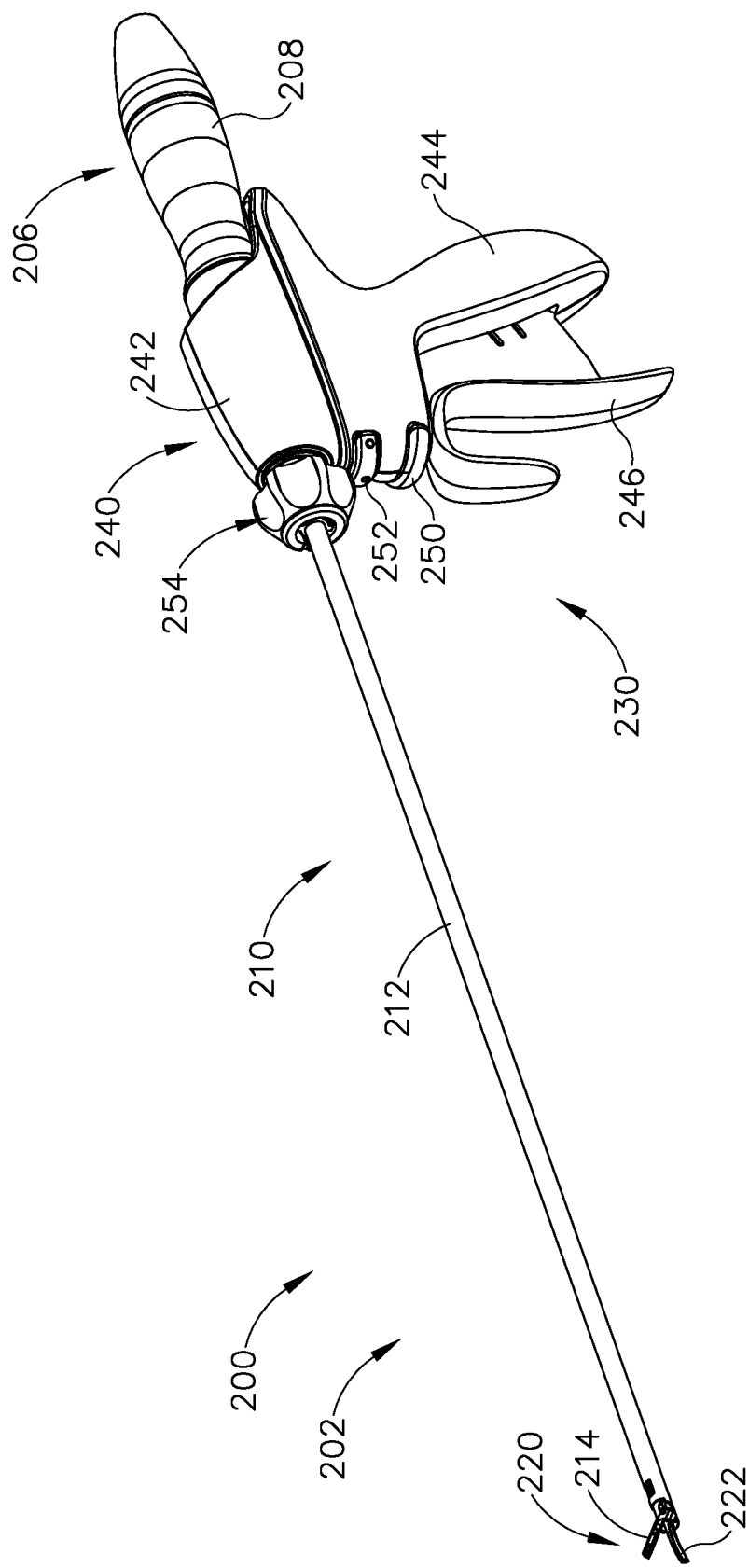
FIG. 2 depicts a perspective view of another exemplary ultrasonic surgical instrument, having a partially disposable assembly and a reusable assembly.
Figure 3:
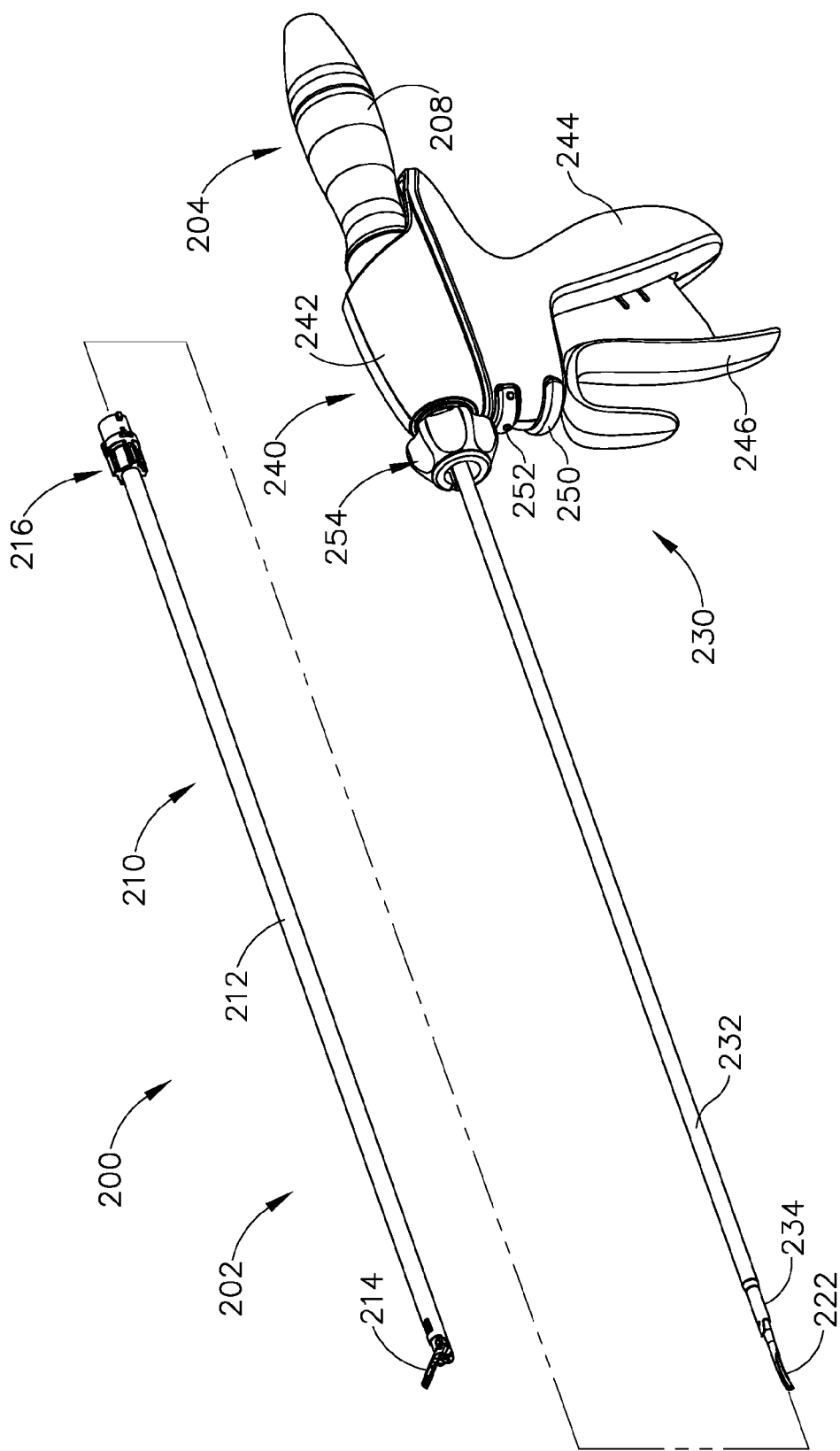
FIG. 3 depicts a partially exploded view of the ultrasonic surgical instrument of FIG. 2, with a disposable sub-assembly separated from a reusable sub-assembly.

FIGS. 2-3 show an exemplary variation of instrument (110) in the form of ultrasonic surgical instrument (200). Except as otherwise described below, ultrasonic surgical instrument (200) may be configured and operable just like instrument (110) described above and/or in accordance with any of the various teachings of the various patent references cited herein. Surgical instrument (200) is configured to be readily broken down into disposable and reusable components. In particular, surgical instrument (200) of this example comprises a reusable assembly (204) and a partially disposable assembly (202). When fully assembled, surgical instrument (200) provides an end effector (220) that includes an ultrasonic blade (222) and a clamp arm (214), which is pivotable toward and away from ultrasonic blade (222). End effector (220) is thus operable to grasp, ultrasonically seal, and ultrasonically sever tissue as described herein and as described in various references cited herein.

Reusable assembly (204) comprises an ultrasonic transducer (208), which is operable to convert electrical power into ultrasonic vibrations, also as described herein and as described in various references cited herein. Ultrasonic transducer (208) is acoustically coupled with ultrasonic blade (222) via an acoustic waveguide (234), a portion of which is shown in FIG. 3. It should be understood that ultrasonic transducer (208), ultrasonic blade (222), and acoustic waveguide (234) may be configured in accordance with the teachings of any of the various references cited herein; or in any other suitable fashion.

Partially disposable assembly (202) of the present example comprises a disposable sub-assembly (210) and a reusable sub-assembly (230). Sub-assemblies (210, 230) are configured to be coupled together to form partially disposable assembly (202), which may then be coupled with reusable assembly (204) for form a complete ultrasonic surgical instrument (200). As shown in FIG. 3, disposable sub-assembly (210) comprises an outer tube (212). Clamp arm (214) is pivotally coupled with a distally projecting tongue of outer tube (212). A coupling member (216) is fixedly secured to the proximal end of outer tube (212). Disposable sub-assembly (210) further comprises a distal inner tube member (not shown), which is slidably and coaxially disposed within the distal end of outer tube (212). This distal inner tube member is also pivotally coupled with clamp arm (214) via a distally projecting tongue of the distal inner tube member. Thus, when outer tube (212) translates longitudinally relative to the distal inner tube member, clamp arm (214) will pivot toward and away from ultrasonic blade (222).

Reusable sub-assembly (230) of the present example comprises a handle assembly (240), a proximal inner tube member (232), acoustic waveguide (234), and ultrasonic blade (222). Proximal inner tube member (232) is configured to removably couple with the distal inner tube member of disposable sub-assembly (210) first when sub-assemblies (210, 230) are assembled together. When proximal inner tube member (232) is coupled with the distal inner tube member of disposable sub-assembly (210), inner tube members (232) remain longitudinally stationary relative to handle assembly (240).

Handle assembly (240) comprises a housing (242) that defines a pistol grip (244). Handle assembly (240) further includes a trigger (246) that is pivotable toward and away from pistol grip (244); and a pair of buttons (250, 252). Buttons (250, 252) are operable to activate ultrasonic transducer (208) to thereby activate ultrasonic blade (222). In particular, one button (250) will provide activation of ultrasonic blade (222) at one power level or profile; while the other button (252) will provide activation of ultrasonic blade (222) at another power level or profile. Of course, any other suitable user input feature(s) may be used. It should also be understood that handle assembly (240) may be modified to include a feature that is operable to activate RF electrosurgical energy at end effector (220) (e.g., like button (125) described above).

Trigger (246) is operable to actuate clamp arm (214), such that clamp arm (214) will pivot toward ultrasonic blade (222) when trigger (246) us pivoted toward pistol grip (244); and such that clamp arm (214) will pivot away from ultrasonic blade (222) when trigger (246) us pivoted away from pistol grip (244). In the present example, this movement is provided by translating outer tube (212) longitudinally relative to housing (242) in response to pivotal movement of trigger (246), while inner tube members (232) remain longitudinally stationary relative to housing (242). Various suitable ways in which outer tube (212) may be translated longitudinally in response to pivotal movement of trigger (246) will be apparent to those of ordinary skill in the art in view of the teachings herein. It should also be understood that, in some alternative versions, clamp arm (214) is pivoted by translating inner tube members (232) longitudinally relative to housing (242) while outer tube (212) remains longitudinally stationary relative to housing (242).

As shown in FIGS. 2-3, handle assembly (240) of the present example further includes a knob member (254). Knob member (254) is rotatable relative to housing (242). When instrument (200) is fully assembled, knob member (254) is coupled with acoustic waveguide (234), inner tube members (232), and outer tube (212) such that these components will rotate together unitarily relative to housing (242). Knob member (254) also provides guidance to disposable sub-assembly (210) when disposable sub-assembly (210) is being coupled with reusable sub-assembly (230). By way of example only, knob member (254) may be configured and operable in accordance with the teachings of any of the various references cited herein.

After ultrasonic surgical instrument (200) is used in a surgical procedure, reusable assembly (204) may be removed from partially disposable assembly (202). After reusable assembly (204) is removed from partially disposable assembly (202), disposable sub-assembly (210) is then be removed from reusable sub-assembly (230). Reusable assembly (204), disposable sub-assembly (210), and reusable sub-assembly (230) may then be subject to different kinds of processing. Examples of such subsequent processing are described below, while other examples will be apparent to those of ordinary skill in the art in view of the teachings herein.

In some instances, reusable assembly (204) may be cleaned, sterilized, and re-used up to 100 times (by way of example only). Disposable sub-assembly (210) may be disposed of immediately, such that disposable sub-assembly (210) is only used in one single surgical procedure. Reusable sub-assembly (230) may be cleaned, sterilized, and re-used in different surgical procedures between 2 to 20 times (by way of example only). Of course, these re-use scenarios are merely illustrative examples. It should nevertheless be understood that the configuration of partially disposable assembly (202) may minimize the amount of single-use material that is disposed of after each surgical procedure. It should also be understood that, in some variations, partially disposable assembly (202) is simply disposed of as a single unit. In other words, in some variations, partially disposable assembly (202) is not configured to be disassembled into disposable sub-assembly (210) and reusable sub-assembly (230).

By way of example only, as part of the post-surgery processing for re-use, reusable assembly (204) and/or reusable sub-assembly (230) may be sterilized in a conventional relatively low temperature, relatively low pressure, hydrogen peroxide sterilization process (e.g., in a STERRAD® sterilizing system by Advanced Sterilization Products of Irvine, Calif.). Alternatively, reusable assembly (204) and/or reusable sub-assembly (230) may be sterilized using any other suitable systems and techniques.

In addition to the foregoing, instrument (200) may be constructed and operable in accordance with at least some of the teachings of U.S. patent application Ser. No. 15/270,540, entitled "Ultrasonic Surgical Instrument with Removable Shaft Assembly Portion," filed Sep. 20, 2016, now U.S. Patent Pub. No. 2017/0105753, published Apr. 20, 2017, the disclosure of which is incorporated by reference herein; and/or U.S. patent application Ser. No. 15/270,600, entitled "Ultrasonic Surgical Instrument with Removable Shaft Assembly Portion," filed Sep. 20, 2016, now U.S. Patent Pub. No. 2017/0105751, published Apr. 20, 2017, the disclosure of which is incorporated by reference herein. In addition, or in the alternative, instrument (200) may be constructed and operable in accordance with at least some of the teachings of any of the various patent references cited herein.

III. Exemplary Life Cycle Indicator Assemblies

In some versions, partially disposable assembly (202) and/or reusable assembly (204) includes one or more features that are operable to track usage of the corresponding assembly (202, 204), and selectively restrict operability of the corresponding assembly (202, 204) based on use. For instance, partially disposable assembly (202) and/or reusable assembly (204) may include one or more counting sensors and a control logic (e.g., microprocessor, etc.) that is in communication with the counting sensor(s). The counting sensor(s) may be able to detect the number of times ultrasonic transducer (208) is activated, the number of surgical procedures the corresponding assembly (202, 204) is used in, the number of trigger (246) closures, and/or any other suitable conditions associated with use. In some variations, an EEPROM or similar device is used to track usage of partially disposable assembly (202) and/or reusable assembly (204).

The control logic may track data from the counting sensor(s) and compare the data to one or more threshold values. When the control logic determines that one or more threshold values have been exceeded, the control logic may execute a control algorithm to disable operability of one or more components in the corresponding assembly (202, 204). In instances where the control logic stores two or more threshold values (e.g., a first threshold for number of activations and a second threshold for number of surgical procedures, etc.), the control logic may disable operability of one or more components in the corresponding assembly (202, 204) the first time one of those thresholds is exceeded, or on some other basis.

In versions where a control logic is operable to at least partially disable instrument (200) based on the number of uses, the control logic may also determine whether instrument (200) is currently being used in a surgical procedure, and refrain from disabling instrument (200) until that particular surgical procedure is complete. In other words, the control logic may allow the operator to complete the current surgical procedure but prevent instrument (200) (or portions instrument (200)) from being used in a subsequent surgical procedure. Various suitable forms that counters or other sensors may take will be apparent to those of ordinary skill in the art in view of the teachings herein. Various suitable forms that a control logic may take will also be apparent to those of ordinary skill in the art in view of the teachings herein. Similarly, various suitable control algorithms that may be used to restrict usage of instrument (200) (or portions of instrument (200)) will be apparent to those of ordinary skill in the art in view of the teachings herein.

In some instances, a reusable sub-assembly that is designed to have multiple uses, such as reusable sub-assembly (230) described above, may be configured to automatically stop operating after a predetermined number of re-uses. Therefore, after a predetermined amount of re-uses is counted by a reusable sub-assembly (230), that sub-assembly may no longer work to form a fully operable surgical instrument (200). In such instances, it may be desirable to determine how many uses remain for a specific reusable sub-assembly (230) that is configured to be cleaned, sterilized, and re-used. This may allow an operator to discard a completely used reusable sub-assembly (230) without accidentally cleaning, sterilizing, and attempting to reuse reusable sub-assembly (230). The following examples relate to devices that are operable to determine how many uses remain for a specific reusable sub-assembly (230), before that reusable sub-assembly (230) is cleaned, sterilized, and/or otherwise processed. While the below examples are provided in the context of reusable sub-assembly (230), the below teachings may be readily applied to various other kinds of disposable assemblies and sub-assemblies.

A. Exemplary External Life Cycle Indicator Assembly

Figure 4:
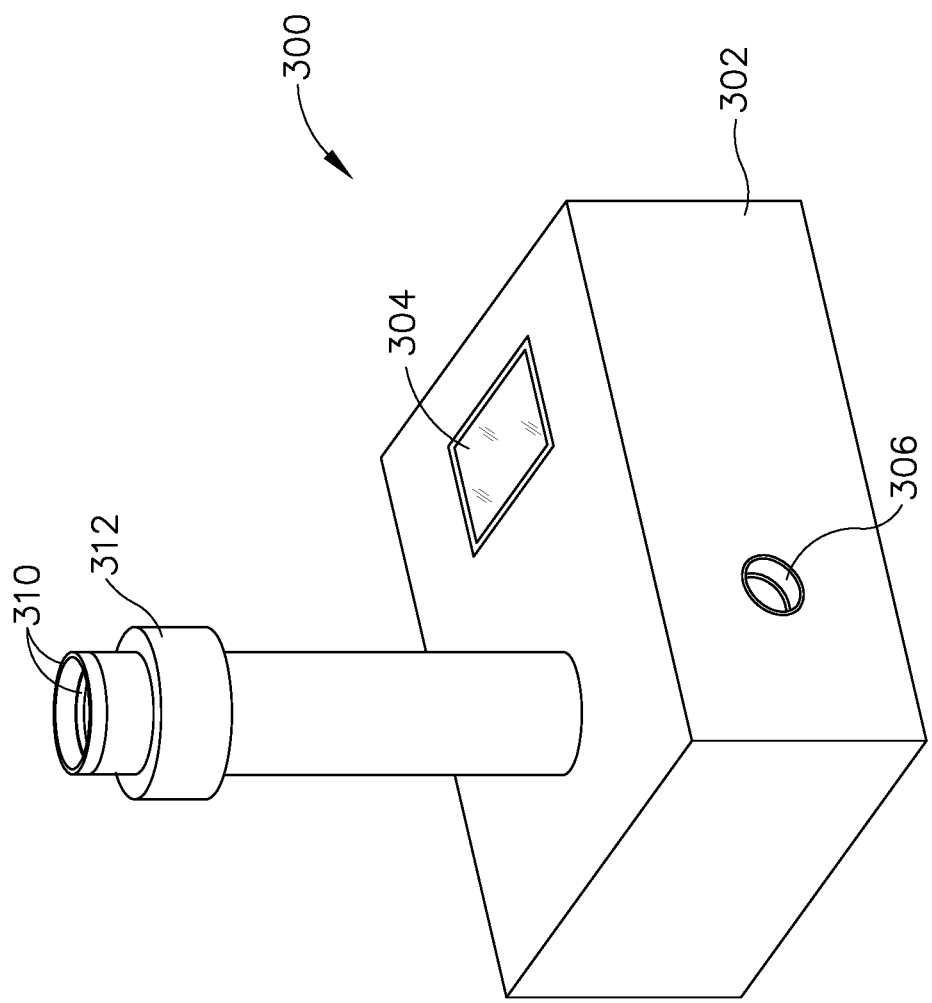
FIG. 4 depicts a perspective view of a multi-use counter machine configured to display the number of uses left for the reusable sub-assembly of FIG. 3.
Figure 5:
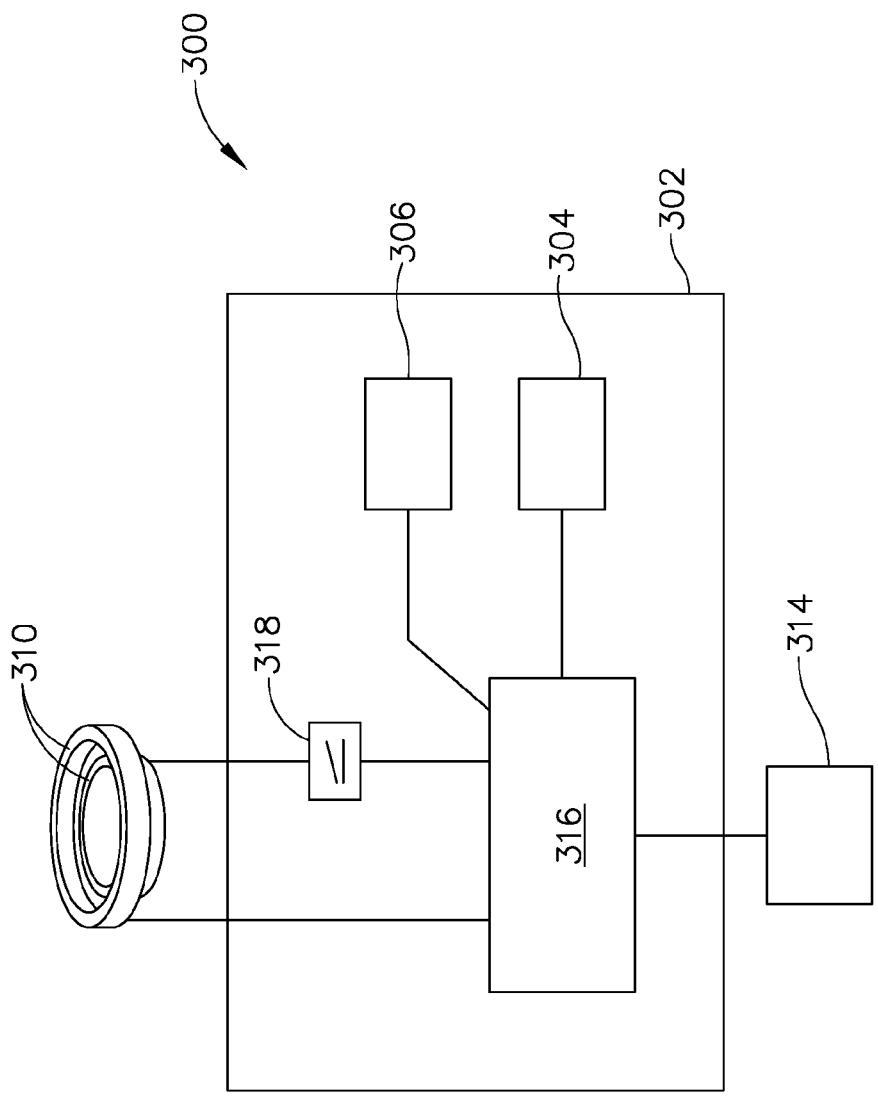
FIG. 5 depicts a schematic view of the multi-use counter machine of FIG. 4.

FIGS. 4-5 show an exemplary multi-use counter (300) that may be selectively connected to a reusable sub-assembly (230) to provide an operator with feedback indicating whether reusable sub-assembly (230) has any remaining uses. As best seen in FIG. 4, the exterior of multi-use counter (300) includes a housing (302) having a display (304), a plug port (306), and an interface tower (312). Interface tower (312) includes contact rings (310). Contact rings (310) are sized, configured, and arranged to mimic contact rings that would be located on a transducer assembly (208) that is coupled with handle assembly (240) during normal use of the assembled surgical instrument (200) in a surgical procedure. As will be described in greater detail below, contact rings (310) and plug port (306) are both configured to connect to second sub-assembly (230) to determine the remaining number times that second sub-assembly (230) may be used. While second sub-assembly (230) is utilized in the current example, multi-use counter (300) may be configured to operate with any other assembly/sub-assembly that is configured to count that number of times that the assembly/sub-assembly has been used.

FIG. 5 shows exemplary circuitry of multi-use counter (300). As shown, housing (302) contains a processing circuit (316), which is in electrical communication with plug port (306), display (304), and a power supply (314). Processing circuit (316) is also in electrical communication with contact rings (310) and a pressure switch (318). Pressure switch (318) and contact rings (310) are also in electrical communication with each other. As will be discussed in greater detail below, processing circuit (316) is configured to read information from reusable sub-assembly (230) to calculate the number of procedures remaining for sub-assembly (230).

Pressure switch (318) is configured to determine if a weight is resting on contact rings (310) or if a force is otherwise being applied to contact rings (310) indicating a coupling between contact rings (310) and reusable sub-assembly (230). If pressure switch (318) determines a sufficient weight is resting on contact rings (310), or that a sufficient force is otherwise being exerted on contact rings (310), pressure switch (318) will indicate the presence of the weight/force to processing circuit (316). Processing circuit (316) will in turn read information from contact rings (310) and then drive display (304) based on the use information received via contact rings (310). Alternatively, plug port (306) is also configured to communicate use information to processing circuit (316) when an external electrical connection is established with plug port (306).

Figure 6:
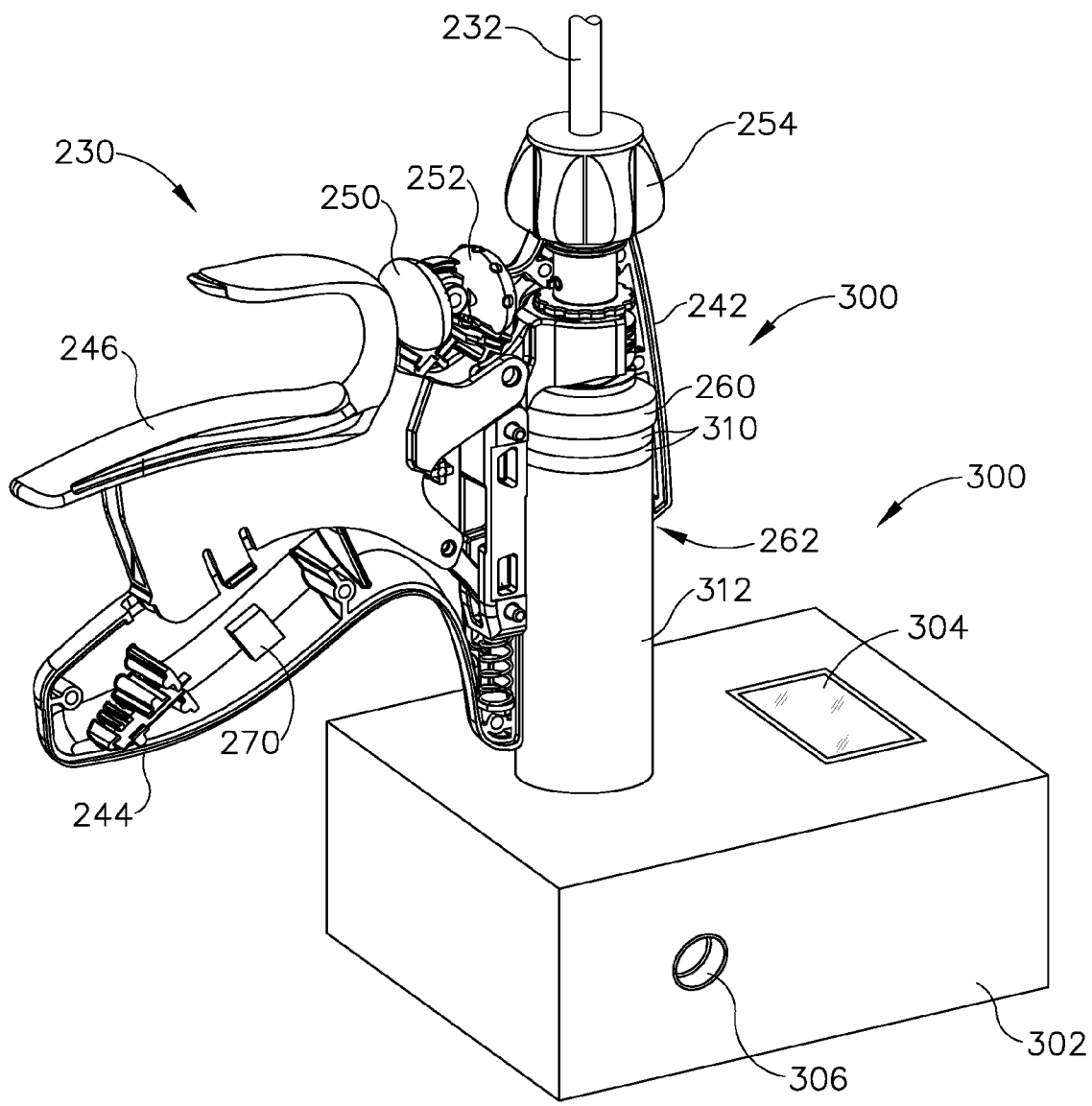
FIG. 6 depicts a perspective view of the reusable sub-assembly of FIG. 3 connected to a first reader of the multi-use counter machine of FIG. 4.

As shown in FIG. 6, handle assembly (240) of reusable sub-assembly (230) includes a counting circuit (270) that is configured to count the number of times that reusable sub-assembly (230) has been used. By way of example only, counting circuit (270) may be configured to count the number of surgical procedures in which reusable sub-assembly (230) has been used, the number of times that buttons (250, 252) have been activated, the number of trigger (246) closures, and/or any other suitable conditions associated with use. Various suitable components that may be incorporated into counting circuit (270) will be apparent to those of ordinary skill in the art in view of the teachings herein. In some versions, handle assembly (240) comprises an EEPROM or other feature that is updated by a generator (116) or controller (118) each time reusable sub-assembly (230) is used in a surgical procedure. In such versions, the EEPROM may constitute (or at least form part of) counting circuit (270).

In some variations where counting circuit (270) includes an EEPROM, the EEPROM may comprise an NFC (Near Field Communication) EEPROM tag with dual power/communication mode operation. By way of example only, such an NFC EEPROM tag may comprise a M24SR02 tag by STMicroelectronics of Geneva, Switzerland. As noted above, generator (116) or controller (118) may write usage tracking data to such an NFC EEPROM. When reusable sub-assembly (230) is in an unpowered state, a conventional NFC reader (e.g., mobile phone or other commercial reader, etc.) may be used to read the NFC EEPROM and thereby obtain usage data.

Handle assembly (240) of the present example also includes a slip ring coupling (260) that is in electrical communication with counting circuit (270). Slip ring coupling (260) is also configured to engage slip rings of ultrasonic transducer (208) to thereby provide electrical continuity between cable (114) and ultrasonic transducer (208) while permitting ultrasonic transducer (208) to rotate relative to cable (114) and relative to housing (242). As noted above, contact rings (310) of interface tower (312) are configured to mimic contact rings of ultrasonic transducer (208). It should therefore be understood that contact rings (310) of interface tower (312) are configured to couple with slip ring coupling (260) of reusable sub-assembly (230), as shown in FIG. 6. Contact rings (310) of interface tower (312) are thereby configured to communicate with counting circuit (270).

To reach the configuration shown in FIG. 6, after reusable assembly (2040 has been removed from handle assembly (240), an operator may simply place interface tower (312) through opening (262) defined by handle assembly (240) such that slip ring coupling (260) makes electrical communication with contact rings (310). At this point, contact rings (310) are in communication with counting circuit (270), and the weight of reusable sub-assembly (230) rests on interface tower (312), thereby activating pressure switch (318). In response to a signal from pressure switch (318) indicating the seating of reusable sub-assembly (230) on interface tower (312), processing circuit (316) reads information from counting circuit (270) via contact rings (310) and slip ring coupling (260).

Processing circuit (316) thereby receives data from counting circuit (270), enabling processing circuit (316) to provide a particular response based on the number of uses indicated by counting circuit (270). By way of example only, processing circuit (316) may provide a response in the form of feedback via display (304). For instance, processing circuit (316) may drive display (304) to display information indicating a particular number of uses remaining for reusable sub-assembly (230). Alternatively, processing circuit (316) may drive display (304) to simply display whether reusable sub-assembly (230) has any remaining uses left (e.g., activating display (304) to illuminate in green if at least one more use remains in reusable sub-assembly (230); or activating display (304) to illuminate in red if no more uses remain in reusable sub-assembly (230)). Various suitable use-related forms of feedback that may be provided via display (304) will be apparent to those of ordinary skill in the art in view of the teachings herein.

Similarly, various suitable forms that display (304) may take will be apparent to those of ordinary skill in the art in view of the teachings herein. It should also be understood that various other kinds of user feedback features may be used, in addition to or in lieu of using display (304). By way of example only, another user feedback feature may include a speaker or other component that is configured to emit audible sound to thereby provide audible feedback to the operator.

Figure 7:
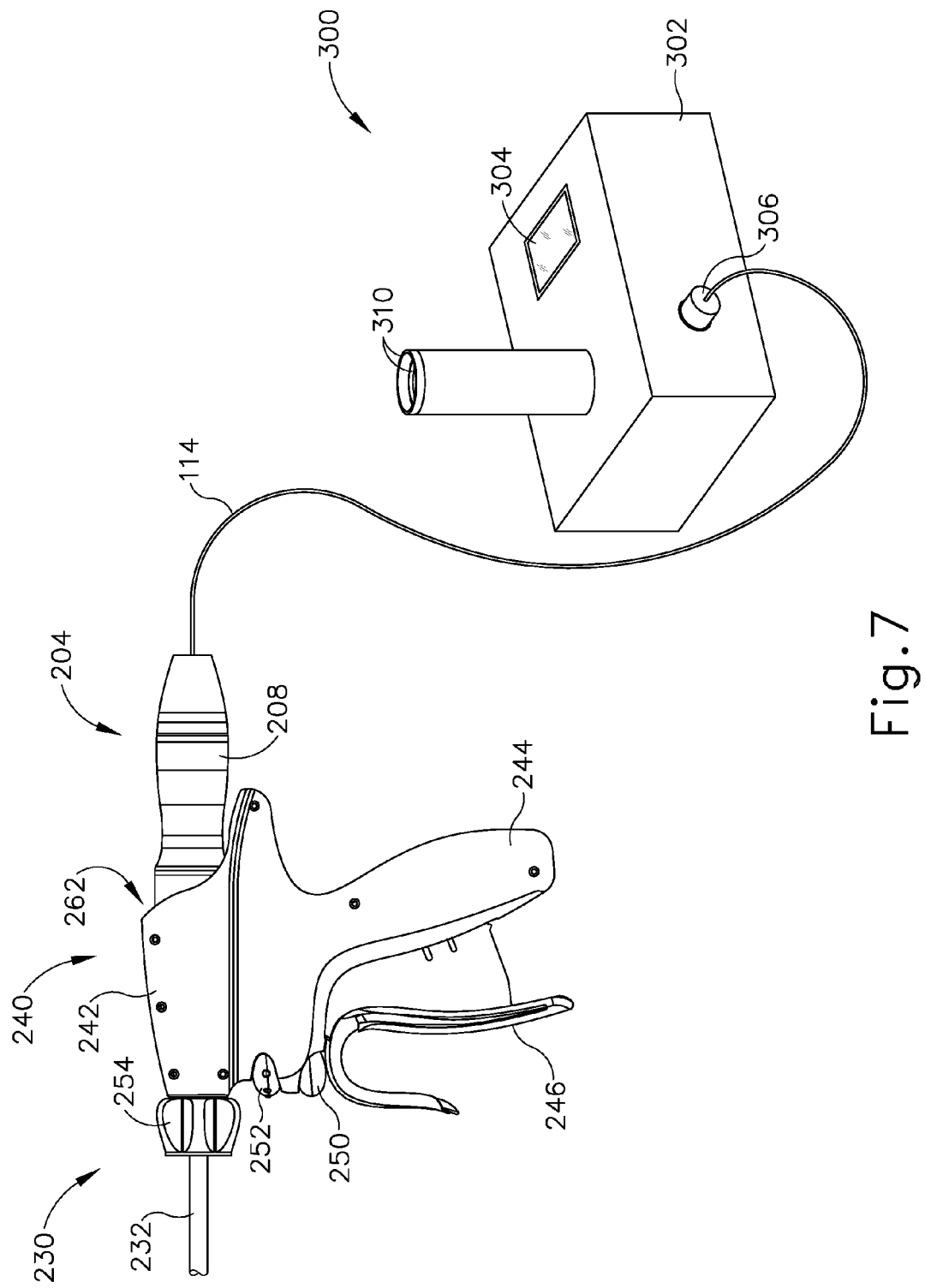
FIG. 7 depicts a perspective view of the reusable assembly of FIG. 2 connected to both the multi-use counter machine of FIG. 4 and the reusable sub-assembly of FIG. 3.

In some other scenarios, reusable assembly (204) may still be connected to reusable sub-assembly (230) when an operator wishes to determine the number of uses remaining for reusable sub-assembly (230). In such scenarios, reusable sub-assembly (230) is in electrical communication with reusable assembly (204) via slip ring coupling (260). Reusable assembly (204) is in communication with counting circuit (270) via slip ring coupling (260) in such scenarios. As illustrated in FIG. 7, an operator may attach a communication cable (114) from reusable assembly (204) to plug port (306) when reusable assembly (204) is still connected to reusable sub-assembly (230). Counting circuit (270) may then communicate information via slip ring coupling (260), reusable assembly (204), and communication cable (114) to plug port (306). Plug port (306) may then transfer this information to processing circuit (316) which then may then drive display (304) based on the number of uses indicated from counting circuit (270) as described above.

While multi-use counter (300) has a combination of contact rings (310) and plug port (314) in the current example, it should be understood multi-use counter (300) may alternatively have only contact rings (310) or only plug port (314) if desired; or have any other suitable interface to read information on counting circuit (270) as would be apparent to one having ordinary skill in the art in view of the teachings herein.

B. Exemplary Integral Life Cycle Indicator Assembly

Figure 8:
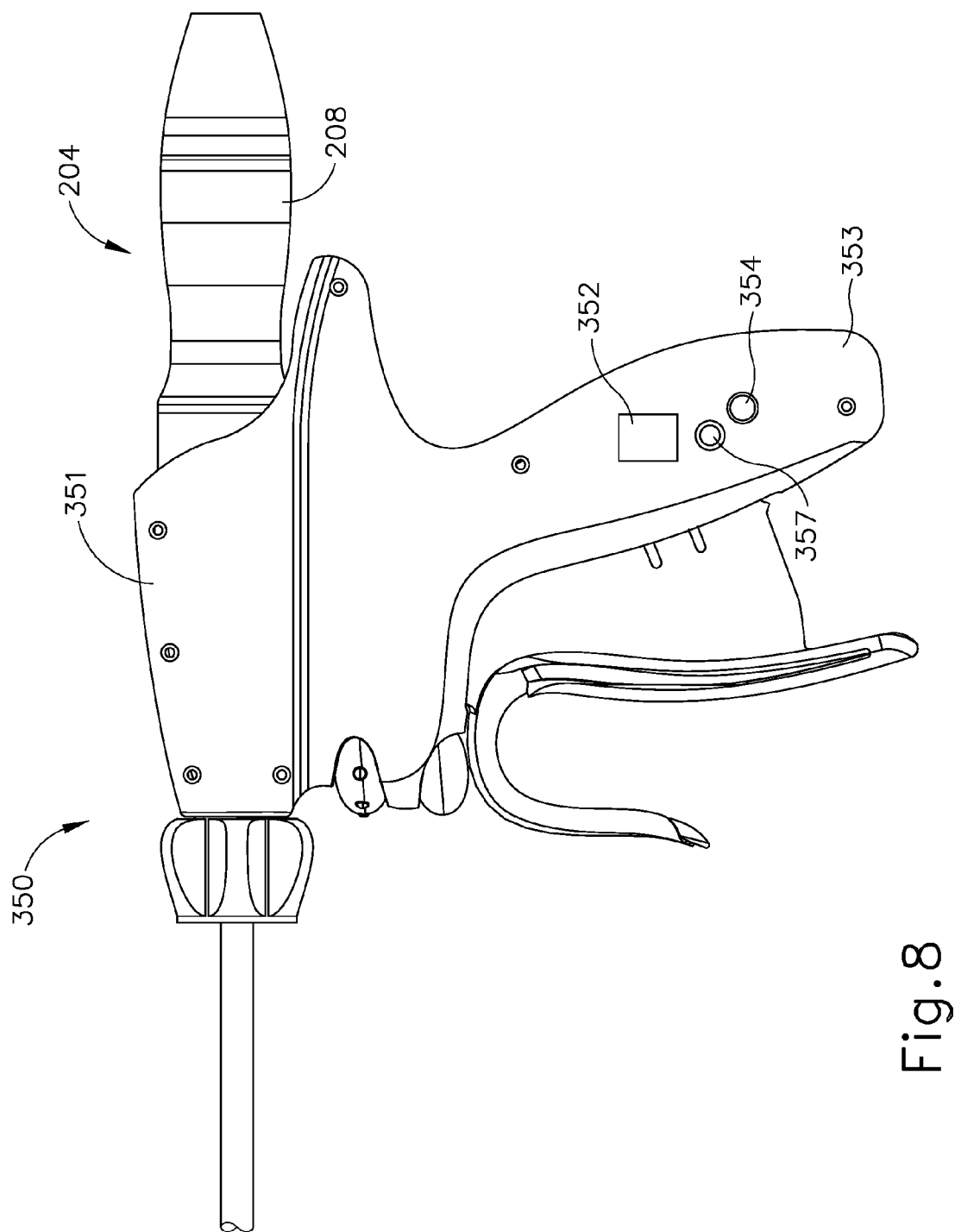
FIG. 8 depicts a side elevational view of an exemplary alternative reusable sub-assembly configured to determine if the reusable sub-assembly has any remaining uses left.

FIG. 8 depicts an exemplary alternative reusable sub-assembly (350) having an integral life cycle indicator assembly. Except as otherwise described below, reusable sub-assembly (350) may be configured and operable just like reusable sub-assembly (230) described above. It should therefore be understood that reusable sub-assembly (350) may be coupled with disposable sub-assembly (210) and reusable assembly (204) to form a variation of instrument (200).

Reusable sub-assembly (350) of the present example includes a body (351) housing a counting circuit (352), a counting circuit activation button (352), and an indicator light (354). Activation button (357) is in electrical communication with counting circuit (352), and counting circuit (352) is in electrical communication with indicator light (354). By way of example only, counting circuit (352) may comprise an EEPROM (e.g., an NFC EEPROM or other kind of EEPROM) as described above. Other suitable components and configurations that may be used to form counting circuit (352) will be apparent to those of ordinary skill in the art in view of the teachings herein. While counting circuit (352), indicator light (354), and activation button (357) are all shown as being positioned in/on pistol grip (353) of body (351), it should be understood that counting circuit (352), indicator light (354), and/or activation button (357) may instead be positioned at any other suitable location(s).

In use, an operator may press activation button (357) to command counting circuit (352) to calculate or otherwise provide the number of remaining uses for reusable sub-assembly (350). If the number is more than zero, indicator light (354) will activate to show the operator that reusable sub-assembly (350) may be used again. By way of example only, indicator light (354) may emit a green light if at least one use remains for reusable sub-assembly (350). If the number is zero, indicator light (354) will activate to show the operator that reusable sub-assembly (350) may not be used again. By way of example only, indicator light (354) may emit a red light if no uses remain for reusable sub-assembly (350).

In the present example, indicator light (354) comprises one or more LEDs, though any other suitable kind of indicator may be used. By way of example only, light (354) may alternatively comprise a display (e.g., an LCD display) showing the number of remaining uses available for reusable sub-assembly (350). Various other suitable kinds of remaining-use indicators will be apparent to those of ordinary skill in the art in view of the teachings herein. It should also be understood that body (351) may further contain a battery (not shown) or other internal power source that is configured to provide the power needed to query counting circuit (352) and illuminate light (354) in response to actuation of activation button (357). Other illustrative examples of integral power sources are described in greater detail below.

Figure 9:
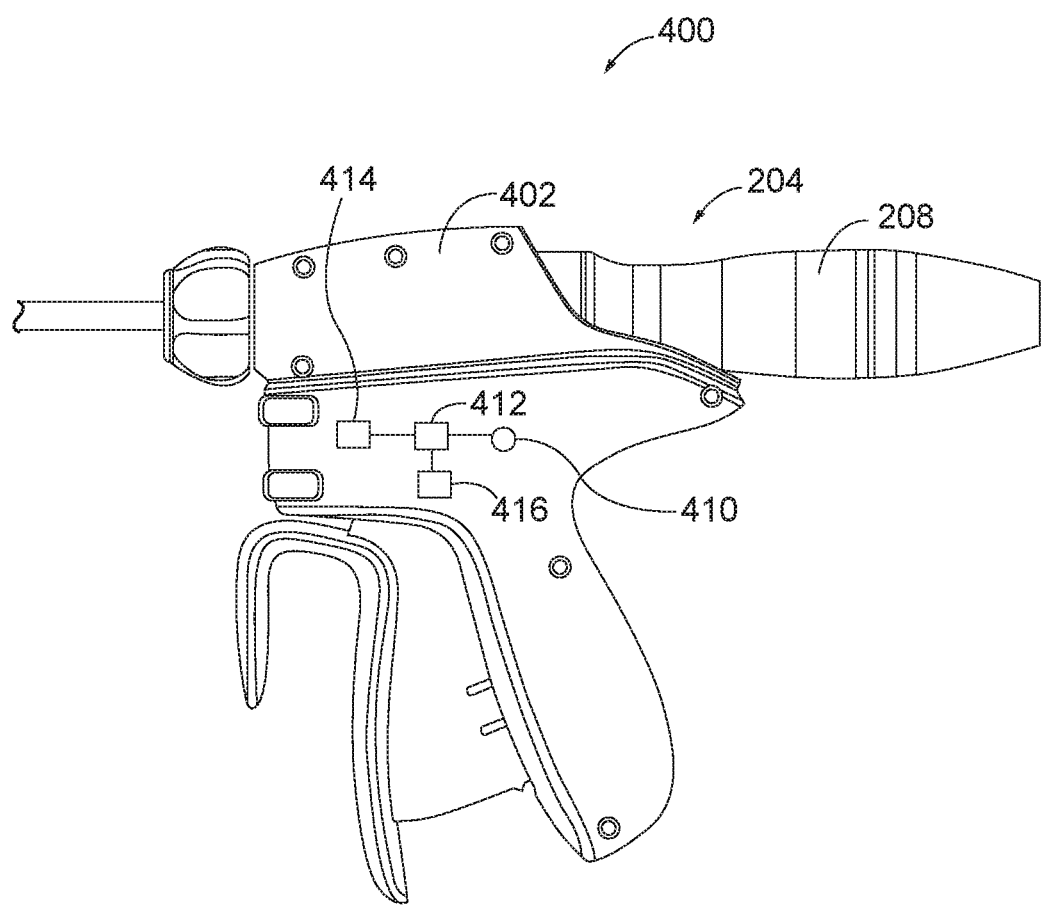
FIG. 9 depicts a side elevational view of another exemplary alternative reusable sub-assembly configured to determine if the reusable sub-assembly has any remaining uses left.

FIG. 9 depicts another exemplary alternative reusable sub-assembly (400) having an integral life cycle indicator assembly. Except as otherwise described below, reusable sub-assembly (400) may be configured and operable just like reusable sub-assembly (230) described above. It should therefore be understood that reusable sub-assembly (400) may be coupled with disposable sub-assembly (210) and reusable assembly (204) to form a variation of instrument (200).

Reusable sub-assembly (400) of the present example includes a body (402) housing a piezoelectric assembly (414), a processing circuit (412), a counting circuit (416), and an indicator light (410). Piezoelectric assembly (414) of the present example is configured to generate a relatively small electrical current in response to an operator manually manipulating piezoelectric assembly (414). By way of example only, piezoelectric assembly (414) may be configured to generate electrical current in response to the operator shaking body (402), in response to the operator pressing a button to actuate a spring-loaded hammer to strike a piezoelectric element (e.g., like a conventional push-button igniter for a gas grill or cigarette lighter, etc.), and/or other forms of manipulation. Additional examples of features that may be used to actuate a piezoelectric element based on manual operator input will be described in greater detail below; while further examples will be apparent to those of ordinary skill in the art in view of the teachings herein.

It should also be understood that the operation of piezoelectric elements in piezoelectric assembly (414) is opposite to the operation of piezoelectric elements in ultrasonic transducer (208). In particular, the piezoelectric elements in piezoelectric assembly (414) are used to generate electrical power in response to mechanical power (e.g., manual actuation by the operator); while the piezoelectric elements in ultrasonic transducer (208) are used to generate mechanical power (i.e., ultrasonic vibrations) in response to electrical power.

Processing circuit (412) is configured to process the electrical power from piezoelectric assembly (414) to drive indicator light (410) based on the usage data stored on counting circuit (416). An exemplary configuration that may be used to form processing circuit (412) will be described in greater detail below; while other suitable configurations will be apparent to those of ordinary skill in the art in view of the teachings herein. By way of example only, counting circuit (416) may comprise an EEPROM (e.g., an NFC EEPROM or other kind of EEPROM) as described above. By way of further example only, processing circuit (412) may comprise a capacitor that is charged by piezoelectric assembly; and discharged to drive indicator light (410). Other suitable components and configurations that may be used to form circuits (412, 416) will be apparent to those of ordinary skill in the art in view of the teachings herein.

In use, an operator may provide manual input to piezoelectric assembly (414), which will energize processing circuit (412) to query counting circuit (416) and illuminate indicator light (410) based on the response from counting circuit (416). If the number is more than zero, indicator light (410) will activate to show the operator that reusable sub-assembly (400) may be used again. By way of example only, indicator light (410) may emit a green light if at least one use remains for reusable sub-assembly (400). If the number is zero, indicator light (410) will activate to show the operator that reusable sub-assembly (400) may not be used again. By way of example only, indicator light (410) may emit a red light if no uses remain for reusable sub-assembly (400).

By way of example only, indicator light (410) may comprise one or more LEDs, though any other suitable kind of indicator may be used. For instance, light (410) may alternatively comprise a display (e.g., an LCD display) showing the number of remaining uses available for reusable sub-assembly (400). Various other suitable kinds of remaining-use indicators will be apparent to those of ordinary skill in the art in view of the teachings herein.

Figure 10:
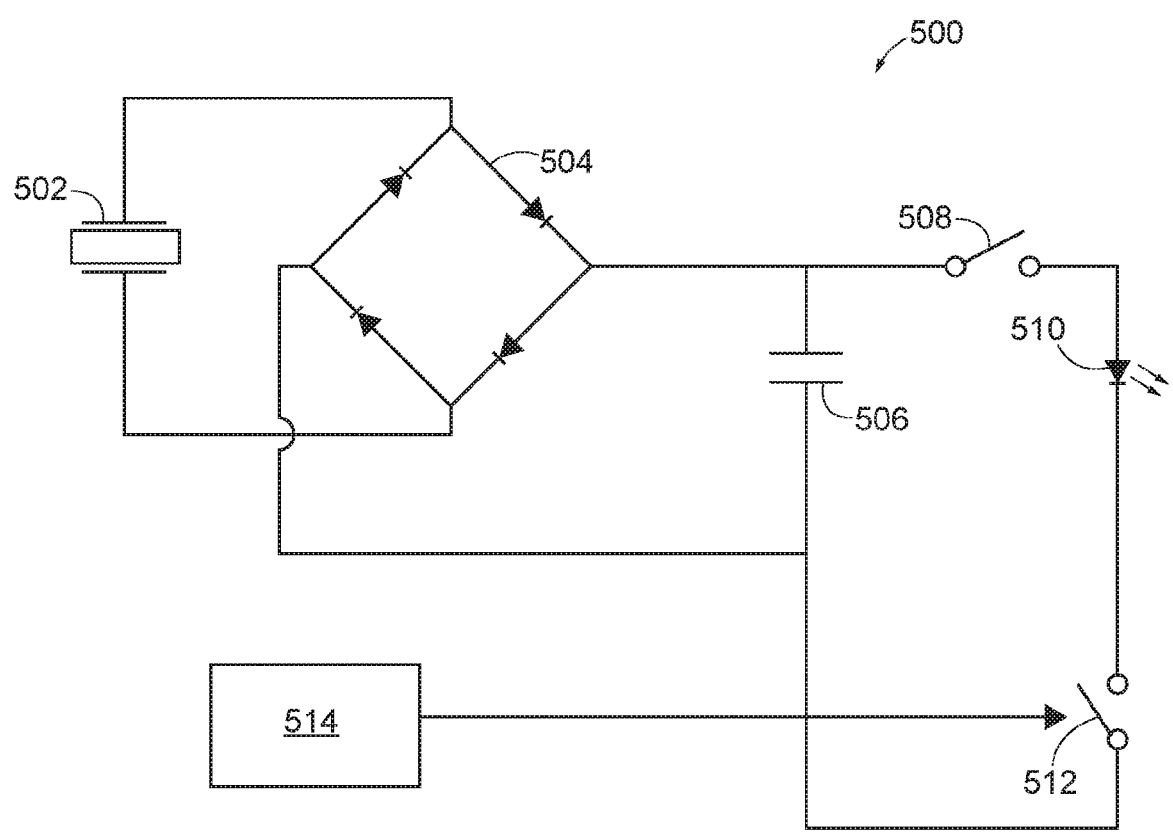
FIG. 10 depicts a schematic view of an exemplary circuit that may be incorporated into the reusable sub-assembly of FIG. 9.

FIG. 10 shows an exemplary circuit (500) that may be used to form processing circuit (412). Circuit (500) of this example comprises a piezoelectric power input (502), a full wave bridge rectifier (504), a capacitor (506), a first switch (508), an LED (510), and a second switch (512). In the context of reusable sub-assembly (400) shown in FIG. 9, piezoelectric assembly (414) may serve as piezoelectric power input (502); and indicator light (410) may serve as LED (510). Full wave bridge rectifier (504) is in communication with piezoelectric power input (502) and is formed by four rectifying diodes that are coupled in series pairs to form a closed loop bridge. Capacitor (506) is also in communication with full wave bridge rectifier (504), such that capacitor (506) is configured to "smooth" the output of full wave bridge rectifier (504) to provide a relatively smooth DC output voltage as is known in the art.

First switch (508) is configured to remain in an open state by default; yet is further configured to transition to a closed state in response to manual operator input. By way of example only, first switch (508) may be resiliently biased to an open state; yet may receive manual input (e.g., via the operator pressing a button, etc.) to transition to a closed state. When first switch (508) is in an open state, LED (510) cannot receive power from full wave bridge rectifier (504); and capacitor (506) will be allowed to charge. When first switch (508) is in the closed state, LED (510) can receive power from full wave bridge rectifier (504). In some variations, first switch (508) is omitted, such that circuit (500) consistently behaves as it would if first switch (508) were in the closed state. In versions where first switch (508) is included, the operator may actuate first switch (508) to cause capacitor (506) to discharge, thereby illuminating LED (510). Thus, the operator may actuate first switch (508) in order to selectively determine whether any uses remain for reusable sub-assembly (400).

Second switch (512) is actuated based on the usage data stored in counting circuit (514). By way of example only, second switch (512) may be in the form of a relay. Other suitable components and configurations that may be used to form second switch (512) will be apparent to those of ordinary skill in the art in view of the teachings herein. By way of further example only, counting circuit (514) may comprise an EEPROM as described above. Other suitable components and configurations that may be used to form counting circuit (514) will be apparent to those of ordinary skill in the art in view of the teachings herein.

In some variations, second switch (512) is configured to remain in an open state until counting circuit (514) indicates that the reusable sub-assembly has been used a maximum number of times. In such versions, LED (510) will remain unilluminated when the operator actuates piezoelectric power input (502) and first switch (508) when there is at least one more available use remaining in the reusable sub-assembly. However, when there are no more available use remaining in the reusable sub-assembly, LED (510) will illuminate (e.g., red) when the operator actuates piezoelectric power input (502) and first switch (508).

In some other versions, LED (510) will illuminate (e.g., green) when the operator actuates piezoelectric power input (502) and first switch (508) when there is at least one more available use remaining in the reusable sub-assembly. However, when there are no more available use remaining in the reusable sub-assembly, LED (510) will remain unilluminated when the operator actuates piezoelectric power input (502) and first switch (508).

As yet another exemplary variation, a second LED (510) may be provided; and second switch (512) may be configured to complete a circuit with either the first LED (510) or the second LED (510) based on the number of uses remaining for the reusable sub-assembly when the operator actuates piezoelectric power input (502). The operator may thus determine whether any uses remain for the reusable sub-assembly based on which LED (510) illuminates in response to actuation of piezoelectric power input (502).

Figure 11:
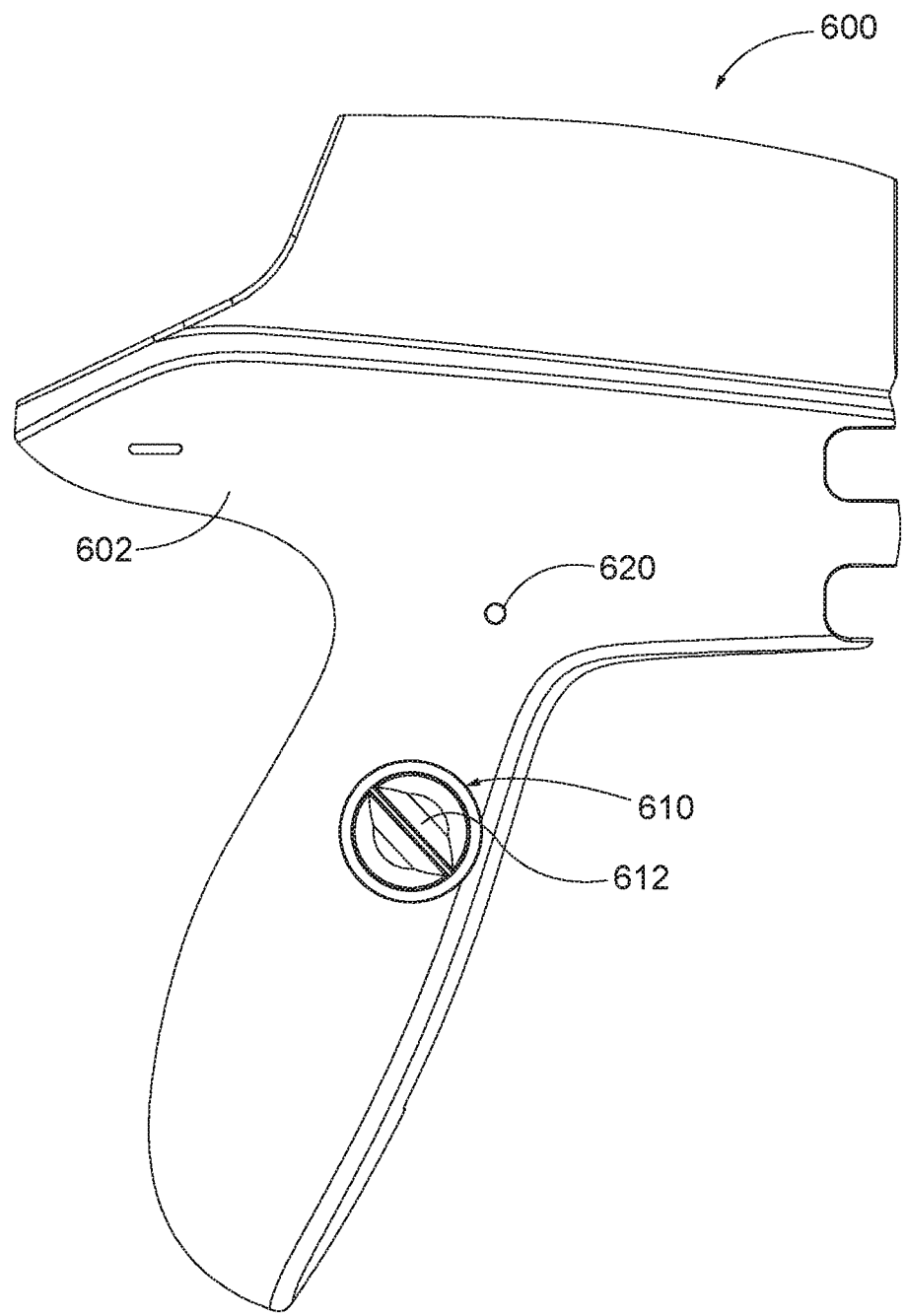
FIG. 11 depicts a side elevational view of a first side of a portion of another exemplary alternative reusable sub-assembly configured to determine if the reusable sub-assembly has any remaining uses left.
Figure 12A:
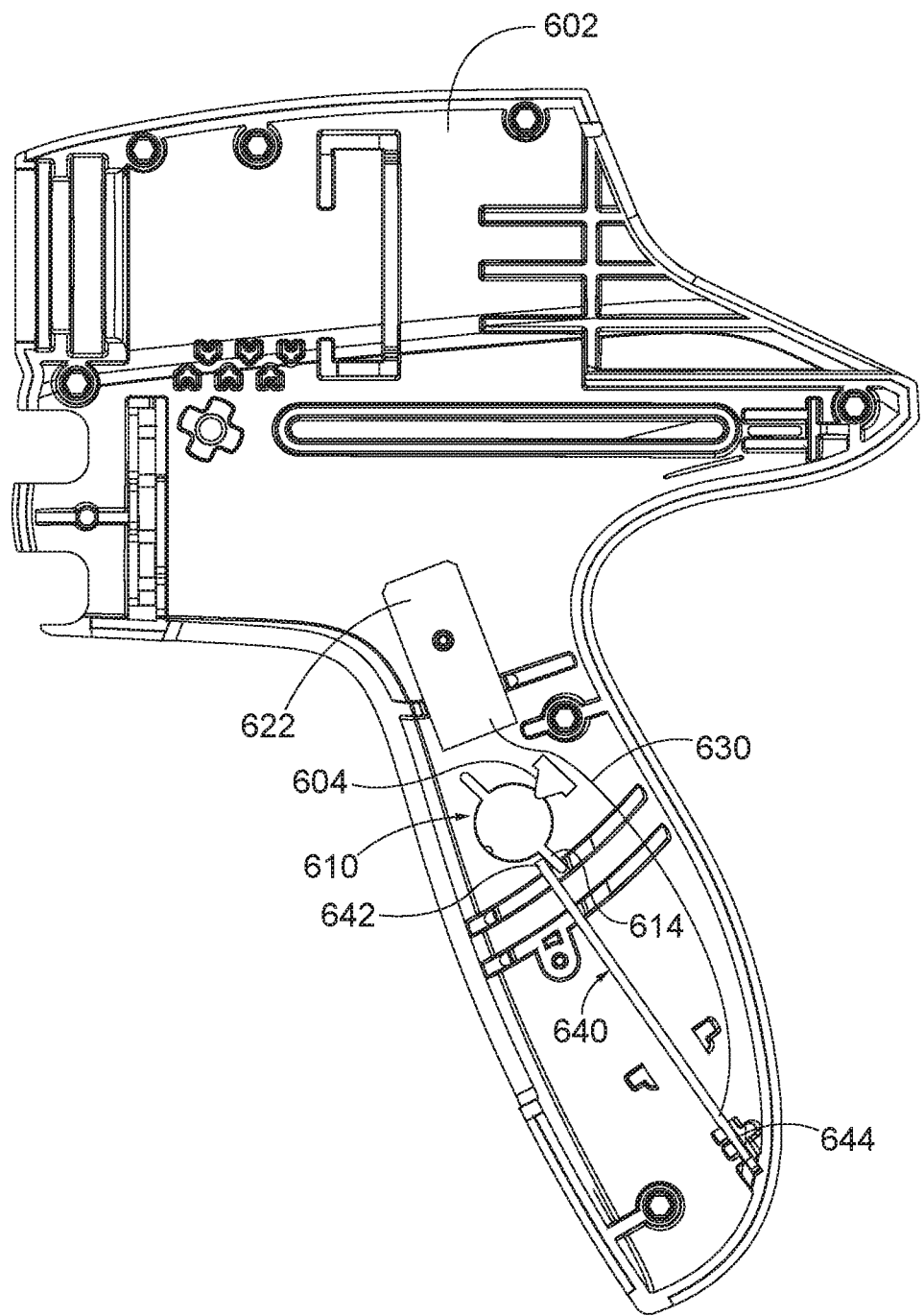
FIG. 12A depicts a side elevational view of a second side of the portion of the reusable sub-assembly of FIG. 11, with a rotary actuator in a first position.
Figure 12B:
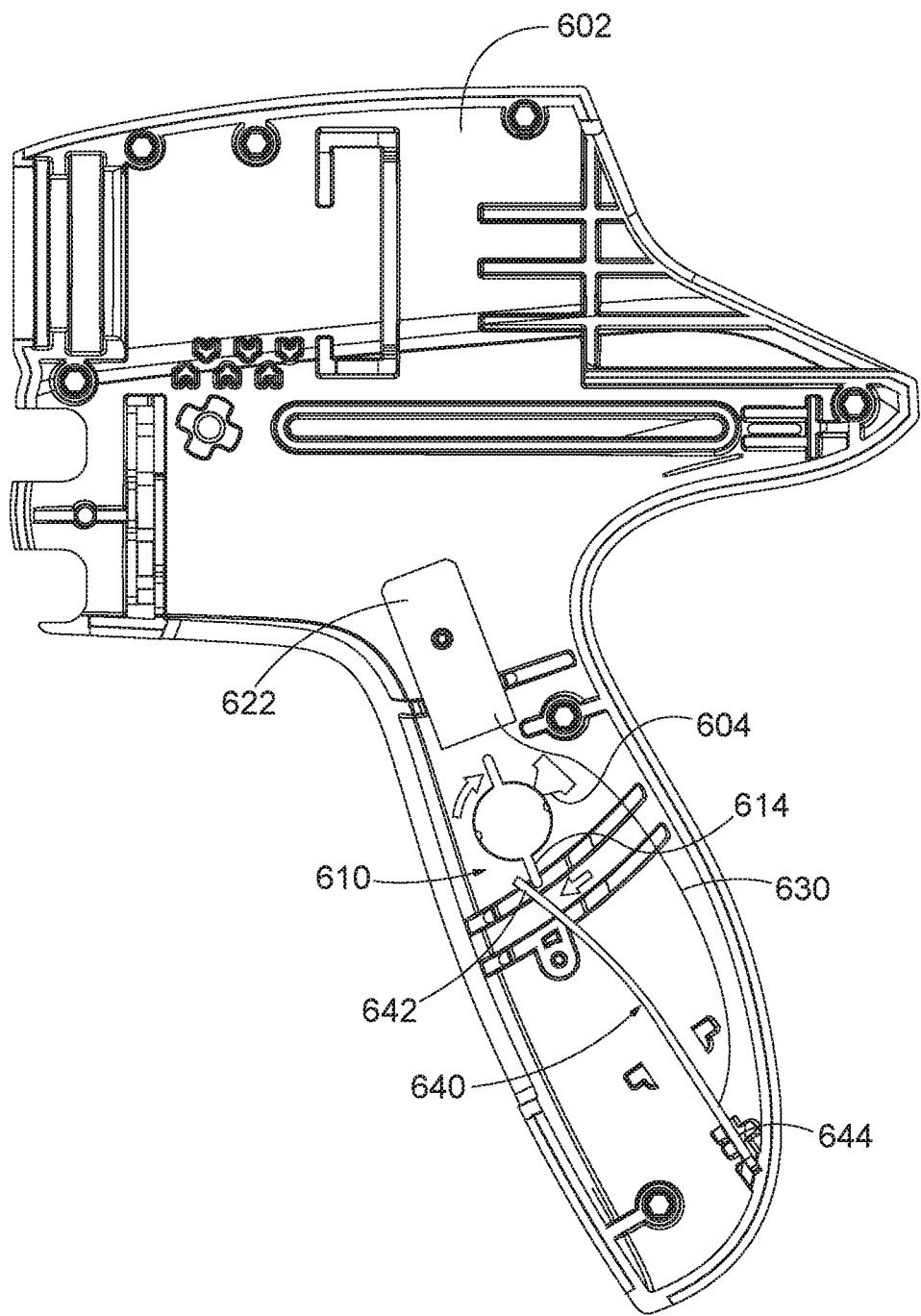
FIG. 12B depicts a side elevational view of a second side of the portion of the reusable sub-assembly of FIG. 11, with the rotary actuator in a second position.
Figure 12C:
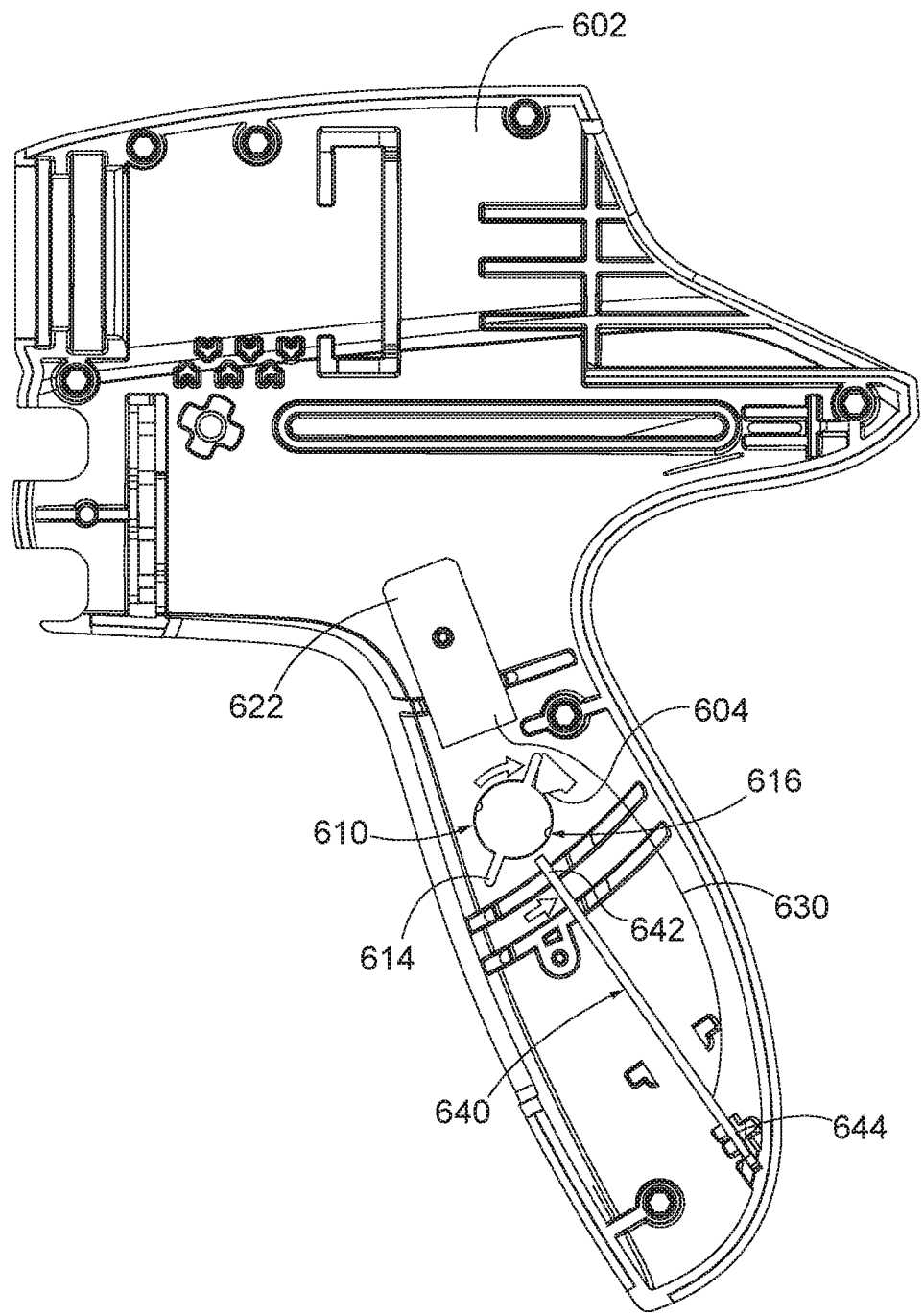
FIG. 12C depicts a side elevational view of a second side of the portion of the reusable sub-assembly of FIG. 11, with the rotary actuator in a third position.
Figure 13:
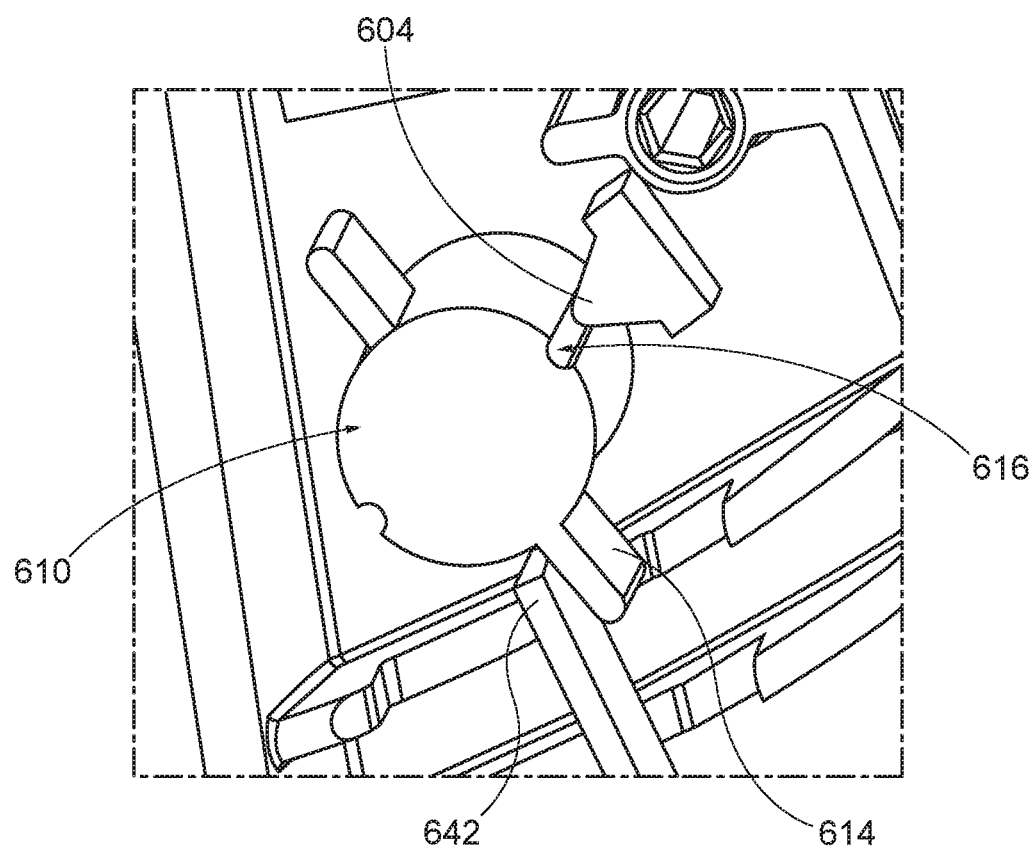
FIG. 13 depicts an enlarged perspective view of the rotary actuator of the reusable sub-assembly of FIG. 11 in the first position of FIG. 12A.

FIGS. 11-12C show an exemplary alternative handle assembly portion (600) that may be readily incorporated into handle assembly (240) to provide features indicating the whether any uses remain for reusable sub-assembly (230). As shown in FIG. 11, handle assembly portion (600) comprises a housing (602) with a rotary actuator (610) and an LED (620). Actuator (610) includes a grip feature (612) that promotes grasping of actuator (610) by an operator, thereby enabling the operator to rotate actuator (610) relative to housing (602). As shown in FIGS. 12A-13, actuator (610) further includes a pair of paddles (614) extending radially outwardly from the central body of actuator (610). In the present example, actuator (610) only has two paddles (614); and paddles (614) are angularly spaced apart from each other by 180°. In some other versions, one single paddle (614) or more than two paddles (614) may be provided at any other suitable spacing.

As also shown in FIGS. 12A-13, actuator (610) includes a pair of longitudinally extending notches (616) formed in the central body of actuator (610). Notches (616) are angularly offset from paddles (614) by 90°, such that notches (616) are angularly spaced apart from each other by 180°. It should be understood that any other suitable number of notches (616) may be used; and notches (616) may have any other suitable positioning and/or relationship with paddles (614). Notches (616) are configured to receive a boss (604), which is formed as a unitary feature of housing (602) in this example. In particular, boss (604) is configured to cooperate with each notch (616) to form a detent assembly. Thus, when boss (604) is disposed in notch (616), boss (604) and notch (616) cooperate to substantially maintain the rotational position of actuator (610) in housing (602), thereby preventing inadvertent rotation of actuator (610) relative to housing (602). However, boss (604) and notch (616) enable intentional rotation of actuator (610) relative to housing (602), upon receipt of sufficient rotary force on actuator (610) to disengage boss (604) from notch (616). In the present example, paddles (614) and boss (604) are longitudinally offset from each other such that paddles (614) and boss (604) are configured to allow actuator (610) to rotate at least 360° about the longitudinal axis of the body of actuator (610). In other words, paddles (614) and boss (604) are configured and positioned such that paddles (614) and boss (604) will not interfere with each other during rotation of actuator (610) relative to housing (602).

Figure 14:
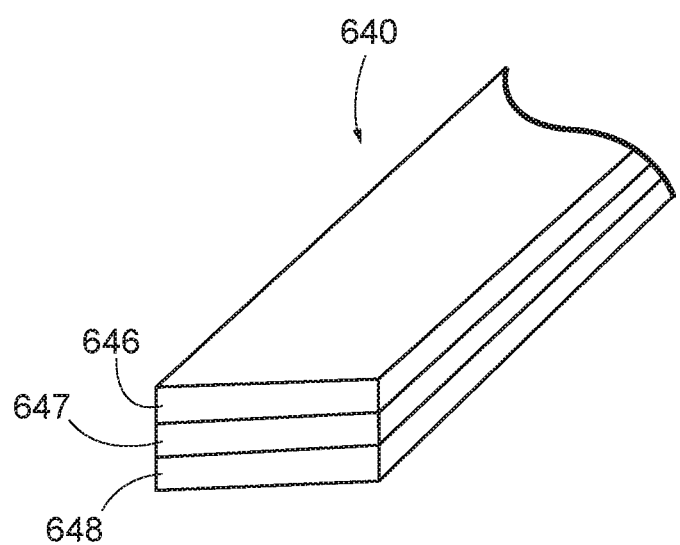
FIG. 14 depicts a partial perspective view of a piezoelectric strip assembly of the reusable sub-assembly of FIG. 11.

As also shown in FIGS. 12A-13, handle assembly portion (600) includes a piezoelectric strip assembly (640). Piezoelectric strip assembly (640) includes a first end (642) and a second end (644). Second end (644) is fixedly secured to housing (602) while first end (642) is substantially free to move relative to housing (602), such that piezoelectric strip assembly (640) is mounted in a cantilevered fashion within housing (602). As shown in FIG. 14, piezoelectric strip assembly (640) further includes a first piezoceramic plate (646), a second piezoceramic plate (648), and a carrier (647). Plates (646, 648) are bonded to carrier (647), thereby forming a bimorph composite assembly. By way of example only, carrier (647) may comprise a polymer, stainless steel, and/or any other suitable material(s) as will be apparent to those of ordinary skill in the art in view of the teachings herein.

Piezoelectric strip assembly (640) is resiliently biased to maintain a straight configuration; yet piezoelectric strip assembly (640) is configured to bend in response to transversely oriented force exerted against first end (642). In particular, as shown in FIGS. 12A-12C, piezoelectric strip assembly (640) is configured and positioned such that paddle (614) will engage first end (642) of piezoelectric strip assembly (640), bend piezoelectric strip assembly (640), then disengage piezoelectric strip assembly (640) as actuator (610) is rotated through a certain angular range of motion. When piezoelectric strip assembly (640) encounters the deformation associated with bending (FIG. 12B), and the return to the straight configuration (FIG. 12C), piezoelectric strip assembly (640) will vibrate. By way of example only, this vibration may be at a frequency up to approximately 1 kHz. When piezoelectric strip assembly (640) vibrates, plates (646, 648) generate electrical power. This electrical power is communicated along a wire (630), which couples piezoelectric strip assembly (640) with a circuit (622). While just one wire (630) is shown, two wires may be used (e.g., one wire for each plate (646, 648)).

LED (620) is part of circuit (622). A counting circuit (not shown) (e.g., like counting circuit (270)) is also part of circuit (622) (or at least in communication with circuit (622)). When piezoelectric strip assembly (640) generates electrical power in response to the operator rotating actuator (610), this electrical power is used to drive circuit (622) to query the counting circuit and illuminate LED (620) based on the number of uses remaining for the reusable sub-assembly that handle assembly portion (600) is part of. By way of example only, LED (620) may illuminate green if at least one use remains for the reusable sub-assembly that handle assembly portion (600) is part of; and red if no uses remain for the reusable sub-assembly that handle assembly portion (600) is part of.

In use, actuator (610) may remain in the position shown in FIG. 12C during a surgical procedure and at all other times up to the point at which an operator wishes to determine how many uses remain for the reusable sub-assembly that handle assembly portion (600) is part of. As noted above, the detent assembly formed by boss (604) and notch (616) will substantially prevent actuator (610) from inadvertently rotating. As shown in FIG. 12A, boss (604), notch (616), and paddles (614) are configured such that paddle (614) is positioned adjacent to first end (642) of piezoelectric strip assembly (640). Paddle (614) is thus staged to engage first end (642) of piezoelectric strip assembly (640) substantially immediately upon rotation of actuator (610). When the operator intentionally rotates actuator (610), paddle (614) deforms piezoelectric strip assembly (640) and then disengages piezoelectric strip assembly (640), as shown in the series represented in FIGS. 12B-12C. This causes piezoelectric strip assembly (640) to vibrate, which in turn causes piezoelectric strip assembly (640) to provide electrical power to circuit (622). The thus powered circuit (622) drives LED (620) to illuminate based on the number of uses remaining for the reusable sub-assembly that handle assembly portion (600) is part of. The operator visually observes LED (620) and either disposes of the reusable sub-assembly or processes the reusable sub-assembly for re-use, based on the feedback provided via LED (620).

Figure 15:
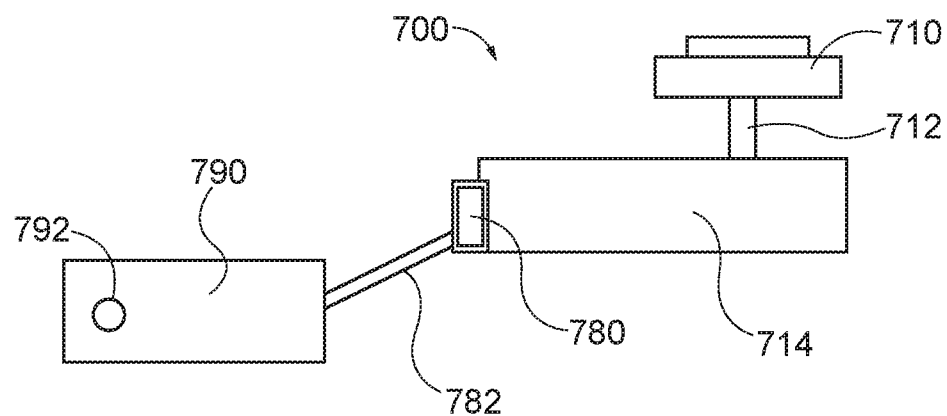
FIG. 15 depicts a side elevational view of an exemplary piezoelectric actuation assembly configured to determine if a reusable sub-assembly has any remaining uses left.
Figure 16:
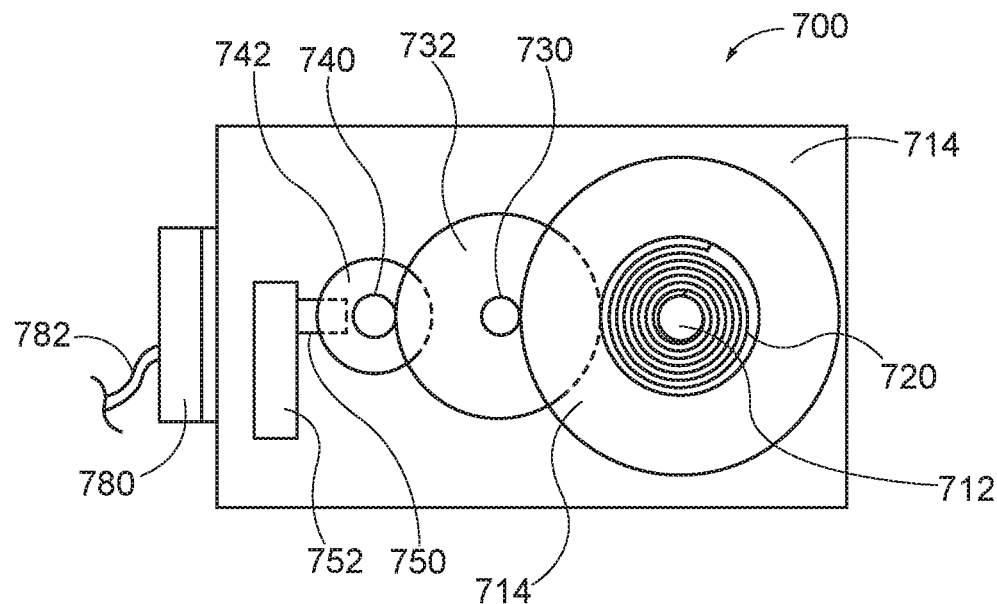
FIG. 16 depicts a top cross-sectional view of the piezoelectric actuation assembly of FIG. 15.
Figure 17:
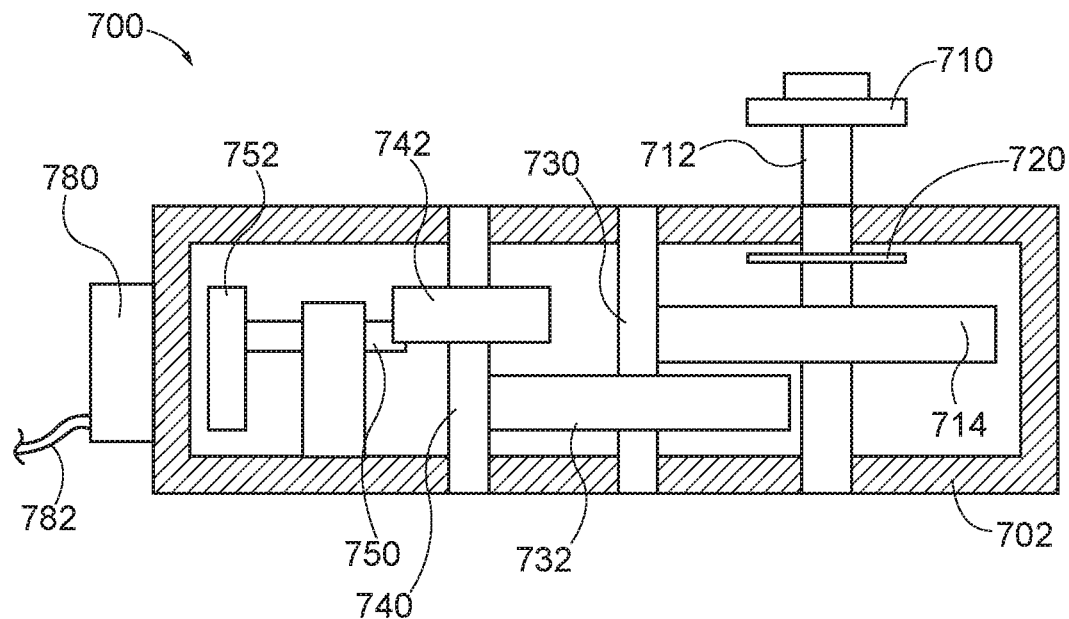
FIG. 17 depicts a side cross-sectional view of the piezoelectric actuation assembly of FIG. 15.

FIGS. 15-17 show yet another exemplary use indicator assembly (700) that may be integrated into any of the various reusable sub-assemblies described herein (among others) to provide an operator with feedback indicating how many uses remain for the reusable sub-assembly. Various suitable ways in which indicator assembly (700) may be integrated into any of the various reusable sub-assemblies described herein (among others) will be apparent to those of ordinary skill in the art in view of the teachings herein. Indicator assembly (700) of this example includes a rotary input knob (710), a housing (702), a piezoelectric element (780), and an indicator circuit (790). Input knob (710) is positioned such that input knob (710) may be grasped and rotated by an operator. A first shaft (712) extends from input knob (710) into housing (702). As best seen in FIGS. 16-17, first shaft (712) is secured to a first gear (714). The outer periphery of first gear (714) includes teeth. A mainspring (720) is also coupled with first shaft (712) and housing (702). Mainspring (720) is configured to impart a rotational bias on first shaft (712), thereby resiliently urging first gear (714) to rotate. A ratchet (not shown) is included to enable winding of mainspring (720) and holding of mainspring (720) in a stressed state until a pawl of the ratchet is released. By way of example only, a button, lever, slider, or other user input feature may be used to selectively release the pawl of the ratchet.

The teeth of first gear (714) mesh with splines on a second shaft (730), which is secured to a second gear (732). Second shaft (730) is rotatably supported by housing (702), thereby enabling rotation of second gear (732) relative to housing (702). The outer periphery of second gear (732) includes teeth. The teeth of second gear (732) mesh with splines on a third shaft (740), which is secured to a third gear (742). Third shaft (740) is rotatably supported by housing (702), thereby enabling rotation of third gear (742) relative to housing (702). The underside (in the view shown in FIG. 17) of third gear (742) includes bevel teeth. The bevel teeth of third gear (742) mesh with bevel teeth on a fourth shaft (750). While shafts (712, 730, 740) are all parallel with each other, fourth shaft (750) is perpendicular to shafts (712, 730, 740) in this example. A mass (752) is eccentrically mounted to fourth shaft (750). Fourth shaft (750) is rotatably supported by housing (702), thereby enabling rotation of mass (752) relative to housing (702). Due to the eccentric mounting of mass (752) to fourth shaft (750), rotation of mass (752) will cause housing (702) to wobble or vibrate.

Piezoelectric element (780) is fixedly secured to housing (702), such that piezoelectric element (780) will wobble or vibrate when housing (702) vibrates. By way of example only, indicator assembly (700) may be configured to provide vibration of piezoelectric element (780) and housing (702) at a frequency of approximately 1 kHz. Piezoelectric element (780) is configured to generate electrical power when piezoelectric element (780) is vibrated due to wobbling or vibration of housing (702). This electrical power is communicated to indicator circuit (790) via wires (782). Indicator circuit (790) includes an LED (792). A counting circuit (not shown) (e.g., like counting circuit (270)) is also part of circuit (790) (or at least in communication with circuit (190)). When piezoelectric element (780) generates electrical power in response to the wobbling or vibration of housing (702), this electrical power is used to drive circuit (790) to query the counting circuit and illuminate LED (792) based on the number of uses remaining for the reusable sub-assembly that indicator assembly (700) is part of. By way of example only, LED (792) may illuminate green if at least one use remains for the reusable sub-assembly that indicator assembly (700) is part of; and red if no uses remain for the reusable sub-assembly that indicator assembly (700) is part of.

In use, indicator assembly (700) may remain idle during a surgical procedure and at all other times up to the point at which an operator wishes to determine how many uses remain for the reusable sub-assembly that indicator assembly (700) is part of. When the operator wishes to determine how many uses remain for the reusable sub-assembly that indicator assembly (700), the operator may rotate knob (710) to thereby wind mainspring (720). The ratchet assembly may hold mainspring (720) in torsional compression when the operator releases knob (710). In some versions, mainspring (720) is fully wound when the operator rotates knob (710) through 360°. After winding mainspring (720), the operator may release the pawl of the ratchet assembly, thereby allowing mainspring (720) to drive rotation of gears (714, 732, 742) and shafts (712, 730, 740, 750) as mainspring (720) unwinds. This rotation rotates mass (752), which causes housing (702) to vibrate, which causes piezoelectric element (780) to vibrate. The vibrating piezoelectric element (780) provides electrical power to circuit (790). The thus powered circuit (790) drives LED (792) to illuminate based on the number of uses remaining for the reusable sub-assembly that indicator assembly (700) is part of The operator visually observes LED (792) and either disposes of the reusable sub-assembly or processes the reusable sub-assembly for re-use, based on the feedback provided via LED (792).

Figure 18:
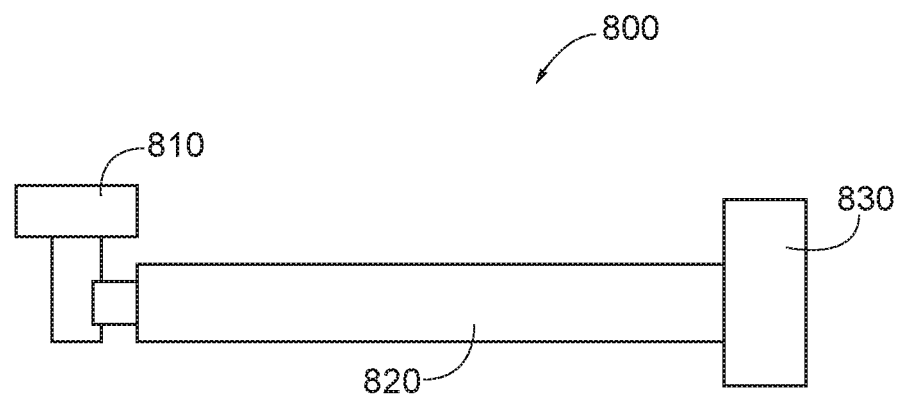
FIG. 18 depicts a side elevational view of another exemplary piezoelectric actuation assembly configured to determine if a reusable sub-assembly has any remaining uses left.
Figure 19A:
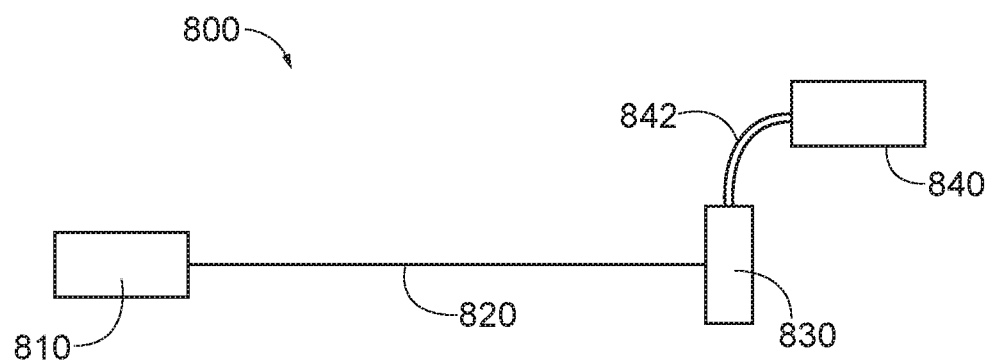
FIG. 19A depicts a top plan view of the piezoelectric actuation assembly of FIG. 18, in a non-actuated state.
Figure 19B:
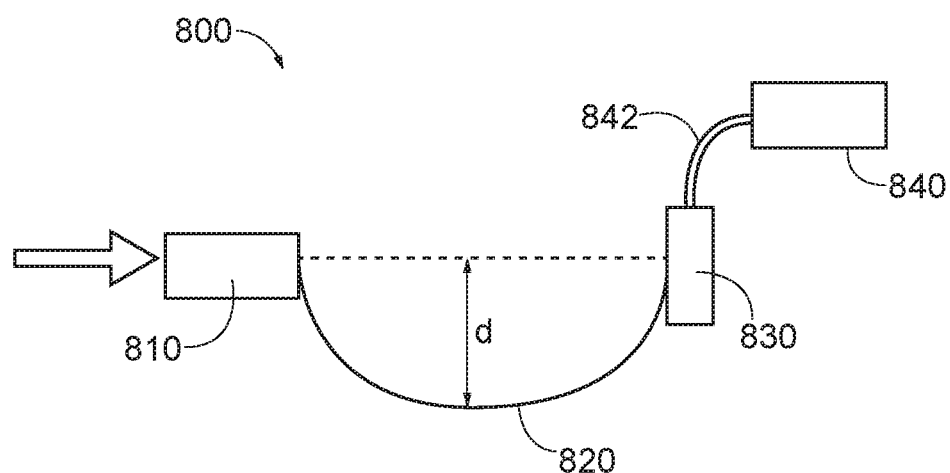
FIG. 19B depicts a top plan view of the piezoelectric actuation assembly of FIG. 18, in an actuated state.

FIGS. 18-19B show yet another exemplary use indicator assembly (800) that may be integrated into any of the various reusable sub-assemblies described herein (among others) to provide an operator with feedback indicating how many uses remain for the reusable sub-assembly. Various suitable ways in which indicator assembly (800) may be integrated into any of the various reusable sub-assemblies described herein (among others) will be apparent to those of ordinary skill in the art in view of the teachings herein. Indicator assembly (800) of this example includes a sliding actuator (810), a piezoelectric strip assembly (820), and a base (830). Sliding actuator (810) is positioned such that sliding actuator (810) may be grasped and translated by an operator. Sliding actuator (810) is fixedly secured to a first end of piezoelectric strip assembly (820). The second end of piezoelectric strip assembly (820) is fixedly secured to base (830), which is configured to provide a mechanical ground for indicator assembly (800). By way of example only, piezoelectric strip assembly (820) may be formed as a bimorph composite assembly just like piezoelectric strip assembly (640) described above.

Piezoelectric strip assembly (820) is resiliently biased to maintain a straight configuration; yet piezoelectric strip assembly (820) is configured to buckle or bend in response to longitudinally oriented compressive forces that are exerted against piezoelectric strip assembly (820). In particular, as shown in FIGS. 19A-19B, piezoelectric strip assembly (820) is configured buckle and thereby bow laterally to a distance (d) from a centerline when sliding actuator (810) is translated toward base (830). By way of example only, indicator assembly (800) may be configured to provide lateral buckling of piezoelectric strip assembly (820) up to approximately 3 to 5 mm in response to translation of sliding actuator (810) toward base (830). When piezoelectric strip assembly (820) encounters the deformation associated with bending (FIG. 19B), piezoelectric strip assembly (820) will generate electrical power. This electrical power is communicated to a circuit (840) via wires (842).

Circuit (840) may include an LED (not shown) and/or any other suitable kind of indicator. Circuit (840) may also include (or be in communication with) a counting circuit as described above. When piezoelectric strip assembly (820) generates electrical power in response to the operator translating sliding actuator (810) toward base (830), the electrical power will drive circuit (840) to query the counting circuit and illuminate LED (or other indicator) based on the number of uses remaining for the reusable sub-assembly that indicator assembly (800) is part of.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a housing; (b) a processing circuit contained within the housing; (c) a user feedback feature in communication with the processing circuit; and (d) a surgical instrument interface feature, wherein the surgical instrument interface feature comprises: (i) a structural interface feature, wherein the structural interface feature is configured to fit in a portion of a body of a surgical instrument, wherein the portion of the body of the surgical instrument is configured to receive an ultrasonic transducer, and (ii) an electrical interface feature, wherein the electrical interface feature is in communication with the processing circuit, wherein the electrical interface feature is configured to interface with a complementary electrical interface feature of the surgical instrument, wherein the complementary electrical interface feature of the surgical instrument is configured to couple with an ultrasonic transducer, wherein the processing circuit is configured to receive data relating to a number of uses of the surgical instrument via the electrical interface feature.

Example 2

The apparatus of Example 1, wherein the processing circuit is further configured to drive the user feedback feature based on the data relating to a number of uses of the surgical instrument.

Example 3

The apparatus of Example 2, wherein the user feedback feature comprises a display.

Example 4

The apparatus of Example 3, wherein the processing circuit is operable to drive the display to present a first color in response to the data indicating that the surgical instrument has at least one remaining use left, wherein the processing circuit is operable to drive the display to present a second color in response to the data indicating that the surgical instrument has no remaining uses left.

Example 5

The apparatus of any one or more of Examples 1 through 4, wherein the structural interface feature comprises a tower.

Example 6

The apparatus of Example 5, wherein the tower is configured to mimic a portion of an ultrasonic transducer.

Example 7

The apparatus of any one or more of Examples 1 through 6, wherein the electrical interface feature comprises one or more electrical contacts exposed on the electrical interface feature.

Example 8

The apparatus of Example 7, wherein the one or more electrical contacts comprise one or more ring contacts.

Example 9

The apparatus of any one or more of Examples 1 through 8, further comprising a sensor in communication with the processing circuit, wherein the sensor is configured to sense coupling of a surgical instrument with the structural interface feature.

Example 10

The apparatus of Example 9, wherein the sensor comprises a pressure switch.

Example 11

The apparatus of any one or more of Examples 9 through 10, wherein the processing circuit is configured to be activated to obtain use data from a surgical instrument via the electrical interface feature in response to the sensor detecting coupling of the surgical instrument with the structural interface feature.

Example 12

The apparatus of any one or more of Examples 1 through 11, further comprising a plug port in communication with the processing circuit.

Example 13

The apparatus of Example 12, wherein the plug port is configured to couple with a cable from an ultrasonic transducer of a surgical instrument.

Example 14

The apparatus of Example 13, wherein the processing circuit is configured to receive data relating to a number of uses of the surgical instrument via the plug port.

Example 15

The apparatus of any one or more of Examples 1 through 14, further comprising a surgical instrument, wherein the surgical instrument comprises: (i) a counting circuit configured to count a number of times that the surgical instrument has been used, (ii) an opening configured to receive the structural interface feature, wherein the opening is further configured to receive an ultrasonic transducer, and (iii) an electrical interface feature in communication with the counting circuit, wherein the electrical interface feature of the surgical instrument is configured to interface with the electrical interface feature of the surgical instrument interface feature.

Example 16

An apparatus, comprising: (a) a body; (b) a shaft assembly extending distally from the body; (c) an end effector located at a distal end of the shaft assembly, wherein the end effector is configured to be activated to thereby operate on tissue; (d) a counting circuit, wherein the counting circuit is configured to store data relating to a number of times the end effector has been activated; (e) a counting circuit activation feature in communication with the counting circuit, wherein the counting circuit activation feature is configured to activate the counting circuit in response to user actuation of the counting circuit activation feature; and (f) a use indicator feature in communication with the counting circuit, wherein the counting circuit is configured to drive the use indicator feature to thereby indicate the number of times the end effector has been activated, in response to user actuation of the counting circuit activation feature.

Example 17

The apparatus of Example 16, wherein the counting circuit activation feature comprises a button.

Example 18

The apparatus of any one or more of Examples 16 through 17, wherein the use indicator feature comprises a light source.

Example 19

A method of using a use indicator device to determine whether a used surgical instrument has any uses remaining, the method comprising: (a) coupling a first portion of the surgical instrument with a structural interface feature of the use indicator device, wherein the first portion of the surgical instrument defines a recess configured to receive an ultrasonic transducer, wherein the first portion of the surgical instrument further includes a first electrical interface feature, wherein the structural interface feature of the use indicator device includes a second electrical interface feature, wherein the first and second electrical interface features are coupled together as a result of the first portion of the surgical instrument being coupled with the structural interface feature of the use indicator device; (b) receiving data relating to prior use of the surgical instrument, wherein the data is received by the use indicator device from the surgical instrument via the coupled first and second electrical interface features; and (c) activating a display of the use indicator device to indicate whether any uses remain for the surgical instrument, based on the received data.

Example 20

The method of Example 19, further comprising removing an ultrasonic transducer from the first portion of the surgical instrument before performing the act of coupling the first portion of the surgical instrument with the structural interface feature of the use indicator device V. Miscellaneous It should be understood that any of the versions of instruments described herein may include various other features in addition to or in lieu of those described above. By way of example only, in addition to the teachings above, it should be understood that the instruments described herein may be constructed and operable in accordance with at least some of the teachings of U.S. Pat. No. 5,322,055; U.S. Pat. No. 5,873,873; U.S. Pat. No. 5,980,510; U.S. Pat. No. 6,325,811; U.S. Pat. No. 6,773,444; U.S. Pat. No. 6,783,524; U.S. Pat. No. 8,623,027; U.S. Pat. No. 8,911,460; U.S. Pat. No. 9,095,367; U.S. Pat. No. 9,393,037; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750, now U.S. Pat. No. 8,623,027, issued Jan. 7, 2014; U.S. Pub. No. 2011/0015660, now U.S. Pat. No. 8,461,744, issued Jun. 11, 2013; U.S. Pub. No. 2012/0112687, now U.S. Pat. No. 9,381,058, issued Jul. 5, 2016; U.S. Pub. No. 2012/0116265; U.S. Pub. No. 2015/0080924; and/or U.S. Pat. App. No. 61/410,603. The disclosures of each of the foregoing patents, publications, and applications are incorporated by reference herein. It should also be understood that the instruments described herein may have various structural and functional similarities with the HARMONIC ACE® Ultrasonic Shears, the HARMONIC WAVE® Ultrasonic Shears, the HARMONIC FOCUS®

Ultrasonic Shears, and/or the HARMONIC SYNERGY® Ultrasonic Blades. Furthermore, the instruments described herein may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the teachings herein relating to the instruments described herein, there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Other types of instruments into which the teachings herein may be incorporated will be apparent to those of ordinary skill in the art.

It should also be understood that any ranges of values referred to herein should be read to include the upper and lower boundaries of such ranges. For instance, a range expressed as ranging "between approximately 1.0 inches and approximately 1.5 inches" should be read to include approximately 1.0 inches and approximately 1.5 inches, in addition to including the values between those upper and lower boundaries.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by an operator immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
   (a) a housing;
   (b) a processing circuit contained within the housing;
   (c) a user feedback feature in communication with the processing circuit;
   (d) a surgical instrument interface feature, wherein the surgical instrument interface feature comprises:
      (i) a structural interface feature, wherein the structural interface feature is configured to fit in a portion of a body of a surgical instrument, wherein the portion of the body of the surgical instrument is configured to receive an ultrasonic transducer, and
      (ii) an electrical interface feature, wherein the electrical interface feature is in communication with the processing circuit, wherein the electrical interface feature is configured to interface with a complementary electrical interface feature of the surgical instrument, wherein the complementary electrical interface feature of the surgical instrument is configured to couple with an ultrasonic transducer, and (e) a plug port in communication with the processing circuit;
  wherein the processing circuit is configured to receive data relating to a number of uses of the surgical instrument via the electrical interface feature, and
  wherein the plug port is configured to couple with a cable from an ultrasonic transducer of a surgical instrument.

2. The apparatus of claim 1, wherein the processing circuit is further configured to drive the user feedback feature based on the data relating to a number of uses of the surgical instrument.

3. The apparatus of claim 2, wherein the user feedback feature comprises a display.

4. The apparatus of claim 3, wherein the processing circuit is operable to drive the display to present a first color in response to the data indicating that the surgical instrument has at least one remaining use left, wherein the processing circuit is operable to drive the display to present a second color in response to the data indicating that the surgical instrument has no remaining uses left.

5. The apparatus of claim 1, wherein the structural interface feature comprises a tower.

6. The apparatus of claim 5, wherein the tower comprises a set of contact of rings, wherein the set of contact rings are sized, configured, and arranged to functionally mimic a set of transducer contact rings of an ultrasonic transducer.

7. The apparatus of claim 1, wherein the electrical interface feature comprises one or more electrical contacts exposed on the electrical interface feature.

8. The apparatus of claim 7, wherein the one or more electrical contacts comprise one or more ring contacts.

9. The apparatus of claim 1, further comprising a sensor in communication with the processing circuit, wherein the sensor is configured to sense coupling of a surgical instrument with the structural interface feature.

10. The apparatus of claim 9, wherein the sensor comprises a pressure switch.

11. The apparatus of claim 9, wherein the processing circuit is configured to be activated to obtain use data from a surgical instrument via the electrical interface feature in response to the sensor detecting coupling of the surgical instrument with the structural interface feature.

12. The apparatus of claim 1, wherein the processing circuit is configured to receive data relating to a number of uses of the surgical instrument via the plug port.

13. The apparatus of claim 1, further comprising a surgical instrument, wherein the surgical instrument comprises:
  (i) a counting circuit configured to count a number of times that the surgical instrument has been used,
  (ii) an opening configured to receive the structural interface feature, wherein the opening is further configured to receive an ultrasonic transducer, and
  (iii) an electrical interface feature in communication with the counting circuit, wherein the electrical interface feature of the surgical instrument is configured to interface with the electrical interface feature of the surgical instrument interface feature.

14. A method of using a use indicator device to determine whether a used surgical instrument has any uses remaining, the method comprising:
  (a) coupling a first portion of the surgical instrument with a structural interface feature of the use indicator device, wherein the first portion of the surgical instrument defines a recess configured to receive an ultrasonic transducer, wherein the first portion of the surgical instrument further includes a first electrical interface feature, wherein the structural interface feature of the use indicator device includes a second electrical interface feature, wherein the first and second electrical interface features are coupled together as a result of the first portion of the surgical instrument being coupled with the structural interface feature of the use indicator device;
  (b) receiving data relating to prior use of the surgical instrument, wherein the data is received by the use indicator device from the surgical instrument via the coupled first and second electrical interface features; and
  (c) activating a display of the use indicator device to indicate whether any uses remain for the surgical instrument, based on the received data.

15. The method of claim 14, further comprising removing an ultrasonic transducer from the first portion of the surgical instrument before performing the act of coupling the first portion of the surgical instrument with the structural interface feature of the use indicator device.

* * * * *